United States Patent [19]
Yamada et al.

[11] Patent Number: 5,739,333
[45] Date of Patent: *Apr. 14, 1998

[54] SULFONAMIDE DERIVATIVE AND PROCESS FOR PREPARING THE SAME

[75] Inventors: Koichiro Yamada; Kōsuke Yasuda; Kohei Kikkawa; Rikako Kohno, all of Saitama-ken, Japan

[73] Assignee: Tanabe Seiyaku Co., Ltd., Osaka, Japan

[*] Notice: The term of this patent shall not extend beyond the expiration date of Pat. No. 5,589,478.

[21] Appl. No.: 644,847

[22] Filed: May 9, 1996

[30] Foreign Application Priority Data

May 16, 1995 [JP] Japan .................... 7-116213
Jun. 16, 1995 [JP] Japan .................... 7-149872

[51] Int. Cl.$^6$ .................... C07D 403/12; C07D 403/14; C07D 413/12
[52] U.S. Cl. .................... 544/296; 544/123; 544/298; 544/319; 544/323; 544/324; 544/325; 544/327; 544/331; 544/332
[58] Field of Search .................... 544/123, 296, 544/298, 319, 323, 324, 325, 327, 331, 332

[56] References Cited

U.S. PATENT DOCUMENTS

| | | | |
|---|---|---|---|
| 3,317,536 | 5/1967 | Grüssner | 260/265.5 |
| 5,270,313 | 12/1993 | Burri et al. | 514/252 |
| 5,292,740 | 3/1994 | Burri et al. | 514/256 |
| 5,589,478 | 12/1996 | Yamada et al. | 514/269 |

FOREIGN PATENT DOCUMENTS

| | | |
|---|---|---|
| 0 569 193 | 11/1993 | European Pat. Off. |
| 0 601 386 | 5/1994 | European Pat. Off. |
| 6 211810 | 8/1994 | Japan |

OTHER PUBLICATIONS

Chemical Abstracts, vol. 121, Abstract No. 230786g (1994).

*Primary Examiner*—Yogendra N. Gupta
*Attorney, Agent, or Firm*—Finnegan, Henderson, Farabow, Garrett & Dunner, L.L.P.

[57] ABSTRACT

Novel sulfonamide derivatives of the formula [I]:

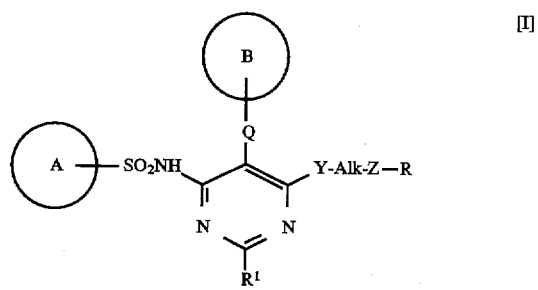

wherein Ring A and Ring B are substituted or unsubstituted monocyclic, bicyclic or tricyclic hydrocarbon, or substituted or unsubstituted heterocyclic group, Q is single bond, —O—, —S—, —SO—, —SO$_2$— or —CH$_2$—, Y is —O—, —S— or —NH—, Alk is lower alkylene or alkenylene, Z is —O— or —NH —, R is substituted or unsubstituted aromatic heterocyclic or aryl, R$^1$ is H, substituted or unsubstituted amino, substituted or unsubstituted lower alkyl, alkenyl, alkynyl, substituted or unsubstituted lower alkylthio, or alkoxy, or substituted or unsubstituted heterocyclic or aryl, or pharmaceutically acceptable salts thereof, which are useful in the prophylaxis or treatment of disorders associated with endothelin activities such as hypertension, pulmonary hypertension, renal hypertension, Raynaud disease, bronchial asthma, gastric ulcer, chronic heart failure, etc.

11 Claims, No Drawings

SULFONAMIDE DERIVATIVE AND PROCESS FOR PREPARING THE SAME

The present invention relates to a novel sulfonamide derivative having endothelin antagonistic activity, and a process for preparing the same.

PRIOR ART

Endothelin is a polypeptide consisting of 21 amino acids which was first isolated from the culture supernatant of porcine aortic endothelial cells. Now, it is known to be a potent vasoconstrictor, bronchoconstrictor and mitogen. It has also been reported that the level of endothelin is significantly increased in the blood of patients with essential hypertension, acute myocardial infarction, pulmonary hypertension, Raynaud disease, diabetes, atherosclerosis, and in the blood and the washing of airway of patients with asthma, compared with that of the normal human being. Thus, endothelin is an endogenous bioactive substance which stimulates durably and directly or indirectly the vascular or non-vascular smooth muscle. The excess production or excess secretion of endothelin seems to be one of the causes for hypertension, pulmonary hypertension, renal hypertension, Raynaud disease, bronchial asthma, gastric ulcer, inflammatory bowl disease (Crohn's disease), shock, carcinogenesis, restenosis after angioplasty, organ dysfunction after transplantation, diabetes, thrombosis, arteriosclerosis, heart failure, acute renal insufficiency, glomerulonephritis, cyclosporin-induced nephrotoxicity, myocardial infarction, angina pectoris, arrhythmia, glaucoma, migraine, cerebrovascular spasm and cerebral infarction. Thus, a compound which strongly antagonizes endothelin has been considered to be useful in the treatment of the above various diseases.

On the other hand, Japanese Patent First Publication (Kokai) Nos. 155864/1993, 222003/1993, 211810/1994 and 17972/1995 disclose as a benzenesulfonamide derivative having endothelin antagonistic activity N-{[5-substituted phenyl (or substituted phenoxy)]-6-hydroxyalkoxypyrimidin-4-yl}-substituted benzenesulfonamides, and the like.

BRIEF DESCRIPTION OF INVENTION

An object of the present invention is to provide a novel sulfonamide derivative having an excellent endothelin antagonistic activity. Another object of the present invention is to provide processes for preparing the same.

DETAILED DESCRIPTION OF INVENTION

The present invention relates to a sulfonamide derivative of the formula [I]:

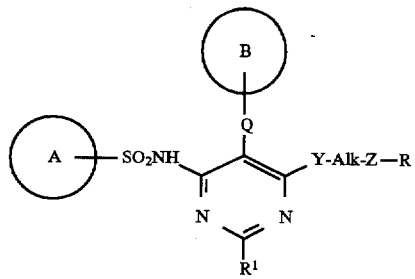

wherein Ring A and Ring B are a substituted or unsubstituted monocyclic, bicyclic or tricyclic hydrocarbon group, or a substituted or unsubstituted heterocyclic group, Q is a single bond or a group of the formula: —O—, —S—, —SO—, —SO$_2$— or —CH$_2$—, Y is a group of the formula: —O—, —S— or —NH—, Alk is a lower alkylene group or a lower alkenylene group, Z is a group of the formula: —O— or —NH—, R is a substituted or unsubstituted aromatic heterocyclic or aryl group, $R^1$ is a hydrogen atom, a substituted or unsubstituted amino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group, or a pharmaceutically acceptable salt thereof.

The hydrocarbon group for Ring A and Ring B includes a partially saturated or completely saturated, monocyclic, bicyclic or tricyclic hydrocarbon group having 3 to 15 carbon atoms. The monocyclic hydrocarbon group is preferably ones having 5 to 8 carbon atoms, more preferably a phenyl group. Suitable examples of other monocyclic hydrocarbon groups are groups of the following formulae:

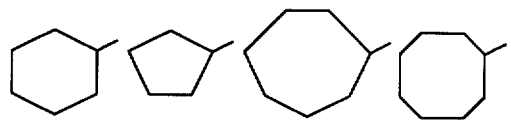

The bicyclic hydrocarbon group is preferably ones having 9 to 11 carbon atoms, more preferably a naphthyl group, an indenyl group, an azulenyl group, or groups of the following formulae:

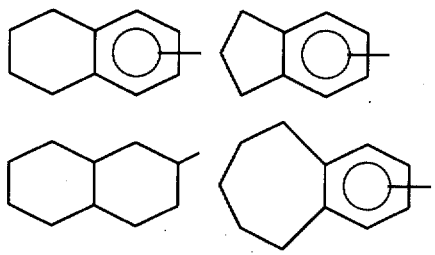

The tricyclic hydrocarbon group is preferably ones having 12 to 15 carbon atoms, more preferably a fluorenyl group, a phenanthryl group, an anthryl group, an acenaphthylenyl group, a biphenylenyl, or groups of the following formulae:

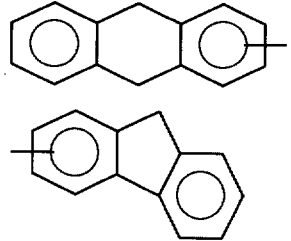

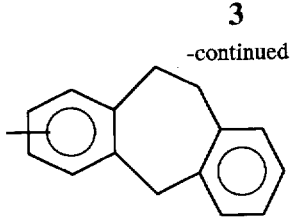

The heterocyclic group for Ring A and Ring B includes a monocyclic, bicyclic or tricyclic, aliphatic, aromatic or a partially saturated aromatic heterocyclic group.

The aromatic heterocyclic group is preferably a monocyclic or bicyclic aromatic heterocyclic group having 1 to 4 heteroatoms selected from a nitrogen atom, an oxygen atom and a sulfur atom, for example, a pyrrolyl group, an imidazolyl group, a furyl group, a thienyl group, a thiazolyl group, an isoxazolyl group, an oxazolyl group, an oxazolinyl group, a pyrazolyl group, a quinazolinyl group, a thienopyrimidinyl group, a pyridyl group, a pyrimidinyl group, pyridazinyl group, a pyrazinyl group, a triazinyl group, a tetrazolyl group, a quinolyl group, an isoquinolyl group, a quinoxalinyl group, a benzothienyl group, a benzothiazolyl group, a benzoxazolyl group or a benzimidazolyl group, or partially saturated groups of these groups.

The partially saturated groups of the aromatic heterocyclic groups are, for example, groups of the following formulae:

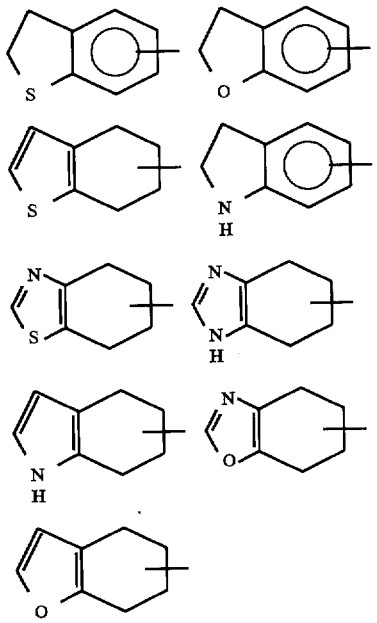

The aliphatic heterocyclic group is preferably a monocyclic or bicyclic aliphatic heterocyclic group having 1 to 4 heteroatoms selected from a nitrogen atom, an oxygen atom and a sulfur atom, for example, a piperazinyl group, a pyrrolidinyl group, a piperidyl group, a homopiperidyl group, a thiomorpholino group, or a morpholino group.

The aromatic heterocyclic group for R includes a monocyclic or bicyclic aromatic heterocyclic group having 1 to 4 heteroatoms selected from a nitrogen atom, an oxygen atom and a sulfur atom, for example, a pyrrolyl group, an imidazolyl group, a furyl group, a thienyl group, a thiazolyl group, an isoxazolyl group, an oxazolyl group, an oxazolinyl group, a pyrazolyl group, a quinazolinyl group, a thienopyrimidinyl group, a pyridyl group, a pyrimidinyl group, a pyridazinyl group, a pyrazinyl group, a triazinyl group, a tetrazolyl group, a quinolyl group, an isoquinolyl group, a quinoxalinyl group, a benzothienyl group, a benzothiazolyl group, a benzoxazolyl group or a benzimidazolyl group, etc.

The heterocyclic group for $R^1$ includes, for example, a monocyclic, bicyclic or tricyclic aliphatic, aromatic or partially saturated aromatic heterocyclic group.

The aromatic heterocyclic group is preferably a monocyclic or bicyclic aromatic heterocyclic group containing 1 to 4 heteroatoms selected from a nitrogen atom, an oxygen atom and a sulfur atom, for example, a pyrrolyl group, an imidazolyl group, a furyl group, a thienyl group, a thiazolyl group, an isoxazolyl group, an oxazolyl group, an oxazolinyl group, a pyrazolyl group, a quinazolinyl group, a thienopyrimidinyl group, a pyridyl group, a pyrimidinyl group, a pyridazinyl group, a pyrazinyl group, a triazinyl group, a tetrazolyl group, a quinolyl group, an isoquinolyl group, a quinoxalinyl group, a benzothienyl group, a benzothiazolyl group, a benzoxazolyl group, a benzimidazolyl group, or partially saturated groups of these groups.

The aliphatic heterocyclic group is preferably a monocyclic or bicyclic aliphatic heterocyclic group having 1 to 4 heteroatoms selected from a nitrogen atom, an oxygen atom and a sulfur atom, for example, a piperazinyl group, a pyrrolidinyl group, a piperidyl group, a homopiperidyl group, a thiomorpholino group, a morpholino group, etc.

The substituent on Ring A and/or Ring B includes, for example, a halogen atom; a protected or unprotected hydroxy group; a lower alkyl group; a lower alkoxy group; a lower alkenyl group; a lower alkynyl group; a lower alkylthio group; a cycloalkyl group; a trifluoromethyl group; a carboxyl group; a cyano group; a tetrazolyl group; a formyl group; a carbamoyl group; a mono- or di-lower alkylaminocarbonyl group; a lower alkoxycarbonyl group; a lower alkoxycarbonyl-lower alkoxy group; a lower alkoxycarbonyl-lower alkyl group; a lower alkoxycarbonyl-lower alkenyl group; a di-lower alkoxy-substituted lower alkyl group; an amino-substituted lower alkyl group; a hydroxy-substituted lower alkyl group; a carboxy-substituted lower alkyl group; a carboxy-substituted lower alkenyl group; a carboxy-substituted lower alkoxy group; a bromopyrimidinyloxy-lower alkyl group; a lower alkylenedioxy group; an aryl-lower alkoxy group; a mono- or di-lower alkylamino group; a lower alkylsulfinyl group; a lower alkylsulfonyl group; a pyridyl group; a nitro group; an imidazole group; an oxazole group; a thiazole group; a triazole group; a furyl group; a phenyl group which may optionally be substituted by 1 to 5 groups selected from a halogen atom, a hydroxyl group, a lower alkyl group, a lower alkoxy group, a lower alkanoyloxy group and a lower alkoxycarbonyloxy group; an arylcarbonylamino group; a carboxy-substituted lower alkanoyloxy-lower alkyl group; or an arylaminocarbonyl group, and the like.

The substituent on the phenyl group for Ring A and/or Ring B is preferably a lower alkyl group or a lower alkoxy group.

Ring A and/or Ring B may optionally have (1) the same or different 1 to 3 substituents of the above mentioned substituents when they are a monocyclic group, or (2) the same or different 1 to 4 substituents of the above mentioned substituents when they are a bicyclic or tricyclic group.

The substituent of the aromatic heterocyclic or aryl group for R includes, for example, a halogen atom; a protected or unprotected hydroxyl group; a nitro group; a cyano group; an amino group; a formyl group; a carboxyl group; a carbamoyl group; an N-lower alkylcarbamoyloxy group; an N-hydroxyiminomethyl group; an N-lower alkoxyiminomethyl group; a lower alkyl group; a hydroxy-substituted lower alkyl group; a cycloalkyl group; a lower alkoxy-lower alkyl group; a lower alkoxycarbonyl-lower alkenyl group; a trifluoro-methyl group; a hydroxy- and aryl-substituted lower alkyl group; a lower alkyl-thio group; a mono- or di-lower alkylamino group; a lower alkanoylamino group; a lower alkoxy group; a lower alkoxy group substituted by a protected or unprotected carboxyl group; an aryloxy group; a lower alkoxycarbonyl group; a lower alkoxy-lower alkenyl group; a lower alkanoyl group; an aryl-carbonyl group; a lower alkenyloxy group; a hydroxy-substituted lower alkynyl group; a lower alkynyl group being optionally protected by a trimethylsilyl group; a cyano-lower alkoxy group; a cycloalkyl-lower alkoxy group; a lower alkylsulfinyl group; a lower alkylsulfonyl group; an aryl group (e.g. phenyl, etc.); a phenyl-lower alkyl group; an aromatic heterocyclic-substituted lower alkyl group; an aromatic heterocyclic-substituted lower alkoxy group; a phenyl-lower alkenyl group; a phenyl-lower alkoxy group; an arylcarbonyl-amino group; an aromatic heterocyclic-substituted hydroxyl group having optionally 1 to 3 substituents selected from a halogen atom and a lower alkyl group; or an aromatic heterocyclic group having optionally a lower alkyl substituent (e.g. thienyl, pyridyl, etc.), and the like.

The aromatic heterocyclic or aryl group for R may optionally have the same or different 1 to 4 substituents of the above mentioned substituents.

The substituent of amino group for $R^1$ includes, for example, a mono- or di-hydroxy-lower alkyl group, a lower alkyl group, a lower alkoxy group, an amino-lower alkyl group, a mono- or di-lower alkylamino-lower alkyl group, a lower alkoxy-lower alkyl group or a carboxy-lower alkyl group, etc. The substituent of the lower alkyl group includes, for example, a halogen atom, a hydroxyl group, a carboxyl group, a lower alkoxycarbonyl group, an aromatic heterocyclic group or an aryl group, etc. The substituent of the lower alkenyl group includes, for example, a lower alkyl group, an amino group, a hydroxyl group, a carboxyl group, etc. The substituent of the lower alkynyl group includes, for example, a carboxyl group, etc. The substituent of the lower alkylthio group includes, for example, a hydroxyl group, a carboxyl group, a lower alkoxycarbonyl group, an amino group or a mono- or di-lower alkyl-amino group, etc. The substituent of the lower alkoxy group includes, for example, a hydroxyl group, a hydroxy-lower alkoxy group, a carboxyl group, a hydroxy-lower alkyl group, a carboxy-lower alkyl group, an amino-lower alkyl group, a mono- or di-lower alkylamino group, etc. The substituent of the heterocyclic group includes, for example, a lower alkyl group, an amino group, a mono- or di-lower alkylamino group, a hydroxyl group, a carboxyl group, etc.

The amino group, the lower alkyl group, the lower alkenyl group, the alkynyl group, the alkylthio group, the lower alkoxy group and/or the heterocyclic group for $R^1$ may have the same or different 1 to 4 substituents of the above mentioned substituents.

The protecting group for hydroxyl group and/or carboxyl group may be any conventional one which can be a protecting group for hydroxyl group and/or carboxyl group, respectively, and the protecting group for hydroxyl group includes, for example, a benzyl group, a methoxymethyl group, a tetrahydropyranyl group, etc., and the protecting group for carboxyl group includes, for example, a methyl group, an ethyl group, a tert-butyl group, a benzyl group, etc.

The aryl group and the aryl moiety of the arylcarbonylamino group, the arylaminocarbonyl group, the aryloxy group and the arylcarbonyl group may be a phenyl group, a lower alkoxyphenyl group or a naphthyl group, etc.

In the sulfonamide derivative [I] of the present invention, Ring A and Ring B are preferably:

1) Ring A is a substituted monocyclic hydrocarbon group, and Ring B is a substituted or unsubstituted bicyclic hydrocarbon group;

2) Ring A is a substituted monocyclic hydrocarbon group, and Ring B is a substituted or unsubstituted heterocyclic group;

3) Ring A is a substituted or unsubstituted bicyclic hydrocarbon group, and Ring B is a substituted monocyclic, bicyclic or tricyclic hydrocarbon group;

4) Ring A is a substituted or unsubstituted bicyclic hydrocarbon group and Ring B is a substituted heterocyclic group;

5) Ring A is a substituted heterocyclic group and Ring B is a substituted or unsubstituted monocyclic, bicyclic or tricyclic hydrocarbon group;

6) Ring A is a substituted heterocyclic group and Ring B is a substituted or unsubstituted heterocyclic group;

7) Ring A is a substituted or unsubstituted heterocyclic group and Ring B is a substituted monocyclic, bicyclic or tricyclic hydrocarbon group;

8) Ring A is a substituted or unsubstituted heterocyclic group and Ring B is a substituted heterocyclic group; and 9) Ring A is a substituted or unsubstituted monocyclic hydrocarbon group, and Ring B is a substituted or unsubstituted monocyclic hydrocarbon group. Among these combinations of Ring A and Ring B, the combinations of 1) Ring A is a substituted monocyclic hydrocarbon group, and Ring B. is a substituted or unsubstituted bicyclic hydrocarbon group, 2) Ring A is a substituted monocyclic hydrocarbon group, and Ring B is a substituted or unsubstituted heterocyclic group, 3) Ring A is a substituted or unsubstituted bicyclic hydrocarbon group, and Ring B is a substituted monocyclic, bicyclic or tricyclic hydrocarbon group, and 4) Ring A is a substituted or unsubstituted monocyclic hydrocarbon group and Ring B is a substituted or unsubstituted monocyclic hydrocarbon group, are preferable, and more preferable one is 1) Ring A is a substituted monocyclic hydrocarbon group, and Ring B is an unsubstituted heterocyclic group, or 2) Ring A is a substituted or unsubstituted monocyclic hydrocarbon group, and Ring B is a substituted or unsubstituted monocyclic hydrocarbon group.

Among the desired compounds [I] of the present invention, the pharmaceutically preferable compounds are compounds of the formula [I] wherein Ring A is a substituted or unsubstituted monocyclic, bicyclic or tricyclic hydrocarbon group or a substituted or unsubstituted heterocyclic group; Ring B is 1) a substituted or unsubstituted bicyclic or tricyclic hydrocarbon group or a substituted or unsubstituted heterocyclic group when Ring A is a substituted or unsubstituted monocyclic hydrocarbon group, or 2) a substituted or unsubstituted monocyclic, bicyclic or tricyclic hydrocarbon group or a substituted or unsubstituted heterocyclic group when Ring A is a substituted or unsubstituted bicyclic or tricyclic hydrocarbon group or a substituted or unsubstituted heterocyclic group; Q is a single bond or a group of the formula: —O—, —S—, —SO—, —SO$_2$— or —CH$_2$—; Y is a group of the formula: —O—, —S— or —NH—; Alk is a lower alkylene group or a lower alkenylene group; Z is a group of the formula: —O— or —NH—; R is a substituted or unsubstituted aromatic heterocyclic or aryl group; $R^1$ is a hydrogen atom, a trifluoromethyl group, a substituted or unsubstituted mono- or di-lower alkylamino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group, or compounds of the formula [I] wherein Ring A and Ring B are a substituted or unsubstituted phenyl group; Q is a single bond or a group of the formula: —O—; Y is a group of the formula: —O—; Alk is an ethylene group; Z is a group of the formula: —O—; R is a substituted or unsubstituted aromatic heterocyclic group; $R^1$ is a substituted or unsubstituted amino group, a substituted or unsubstituted lower alkyl group, a substituted or unsubstituted lower alkoxy group, a substituted or unsubstituted lower alkylthio group or a substituted or unsubstituted heterocyclic group.

The pharmaceutically more preferable compounds are compounds of the formula [I] wherein Ring A is a phenyl group substituted by a lower alkyl group or a lower alkylenedioxy group; Ring B is a naphthyl group, a pyridyl group, a furyl group, a thienyl group being optionally substituted by a lower alkyl group, or a benzothienyl group, or Ring A is a naphthyl group being optionally substituted by a di-lower alkylamino group, an indenyl group, an anthryl group, a thienyl group being optionally substituted by a pyridyl group or a lower alkyl group, a benzofuryl group or a benzothienyl group, and Ring B is a phenyl group being optionally substituted by a lower alkyl group or a lower alkoxy group, a naphthyl group, a pyridyl group, a furyl group, a thienyl group being optionally substituted by a lower alkyl group, or a benzothienyl group; Q is a single bond or a group of the formula: —O—; Y is a group of the formula: —O—; Alk is a lower alkylene group; Z is a group of the formula: —O—; R is a pyrimidinyl group substituted by a group selected from a halogen atom, a thienyl group and a lower alkylthio group; $R^1$ is a hydrogen atom, a hydroxy-substituted lower alkylamino group, a lower alkyl group, a carboxy-substituted lower alkylthio group, a hydroxy-substituted lower alkoxy group, a pyrimidinyl group, a hydroxy-substituted piperidyl group, a lower alkyl-substituted piperazinyl group, or a morpholino group, or compounds of the formula [I] wherein Ring A is a phenyl group substituted by a lower alkyl group; Ring B is a phenyl group substituted by a lower alkyl group or a lower alkoxy group; Q is a single bond or a group fo the formula: —O—; Y is a group of the formula: —O—, Alk is an ethylene group; Z is a group of the formula: —O—; R is a pyrimidinyl group substituted by a group selected from a halogen atom, a lower alkyl group, a hydroxy-lower alkyl group, a lower alkoxy group, a phenyl group, a furyl group, a thienyl group and a pyridyl group; $R^1$ is an amino group which may optionally be substituted by 1 to 2 groups selected from a mono- or di-hydroxy lower alkyl group, a lower alkyl group, a lower alkoxy group, an amino-lower alkyl group, a mono- or di-lower alkylamino-lower alkyl group, a lower alkoxy-lower alkyl group and a carboxy-lower alkyl group; a lower alkyl group substituted by a carboxyl group or a hydroxyl group; a lower alkoxy group which may optionally be substituted by a group selected from a hydroxyl group, a carboxyl group, a hydroxy-lower alkyl group,a carboxy-lower alkyl group, an amino-lower alkyl group and a mono- or di-lower alkyl-amino group; a lower alkylthio group which may optionally be substituted by a group selected from a hydroxyl group, a carboxyl group, a lower alkoxy-carbonyl group, an amino group and a mono- or di-lower alkylamino group; a piperidyl group being optionally substituted by a group selected from a hydroxyl group, a carboxyl group, an amino group and a mono- or di-lower alkylamino group; or a tetrazolyl group.

The pharmaceutically more preferable compounds are compounds of the formula [I] wherein Ring A is a phenyl group substituted by a lower alkyl group or a lower alkylenedioxy group, Ring B is a naphthyl group, a pyridyl group, a furyl group, a thienyl group being optionally substituted by a lower alkyl group, or a benzothienyl group, or Ring A is a naphthyl group being optionally substituted by a di-lower alkylamino group, an indenyl group, an anthryl group, a thienyl group being optionally substituted by a pyridyl group or a lower alkyl group, a benzofuryl group, or a benzothienyl group, Ring B is a phenyl group substituted by a lower alkyl group or a lower alkoxy group, or a thienyl group substituted by a lower alkyl group, Q is a single bond or a group of the formula: —O—, —S—, —SO—, —SO$_2$— or —CH$_2$—; Y is a group of the formula: —O—, —S— or —NH—; Alk is a lower alkylene group or a lower alkenylene group; Z is a group of the formula: —O— or —NH—; R is a substituted or unsubstituted aromatic heterocyclic or aryl group; $R^1$ is a hydrogen atom, a trifluoromethyl group, a substituted or unsubstituted mono- or di-lower alkylamino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group, or compounds of the formula [I] wherein Ring A is a phenyl group substituted by a lower alkyl group; Ring B is a phenyl group substituted by a lower alkyl group or a lower alkoxy group; Q is a single bond or a group of the formula: —O—; Y is a group of the formula: —O—; Alk is an ethylene group; Z is a group of the formula: —O—; R is a pyrimidinyl group substituted by a halogen atom or a lower alkoxy group, $R^1$ is an unsubstituted amino group or an amino group substituted by 1 to 2 groups selected from a mono- or di-hydroxy-lower alkyl group, a mono- or di-lower alkylamino-lower alkyl group and a lower alkoxy-lower alkyl group.

The pharmaceutically much more preferable compounds are compounds of the formula [I] wherein Ring A is a phenyl group substituted by a lower alkyl group, Ring B is a thienyl group being optionally substituted by a lower alkyl group, a naphthyl group, a pyridyl group, a furyl group or a benzothienyl group, or Ring A is a naphthyl group being optionally substituted by a di-lower alkylamino group, or a thienyl group being optionally substituted by a pyridyl group, Ring B is a phenyl group substituted by a lower alkyl group or a lower alkoxy group, Q is a single bond, R is a pyrimidinyl group substituted by a halogen atom or a lower alkylthio group, $R^1$ is a hydrogen atom, a pyrimidinyl group, a morpholino group, or compounds of the formula [I] wherein $R^1$ is an amino group substituted by a hydroxy-lower alkyl group.

The pharmaceutically still further more preferable compounds are compounds of the formula [I] wherein Ring A is a phenyl group substituted by a lower alkyl group, Ring B is a thienyl group being optionally substituted a lower alkyl group, a naphthyl group or a benzothienyl group, or Ring A is a naphthyl group, and Ring B is a phenyl group substituted by a lower alkyl group.

Among the desired compounds [I] of the present invention, other preferable compounds are compounds of the formula [I] wherein Ring A is a phenyl group substituted by a lower alkyl group, Ring B is a thienyl group, or Ring A is a naphthyl group or a thienyl group, Ring B is a phenyl group substituted by a lower alkoxy group, Q is a single bond or a group of the formula: —O—, Y is a group of the formula: —O—, Alk is a lower alkylene group, Z is a group of the formula: —O—, R is a pyrimidinyl group being optionally substituted by a halogen atom or a thienyl group, and $R^1$ is a lower alkyl group, a morpholino group, a lower alkyl-substituted piperazinyl group, or a pyrimidinyl group, or compounds of the formula [I] wherein Ring A is a phenyl group substituted by a lower alkyl group, Ring B is a phenyl group substituted by a lower alkyl group or a lower alkoxy group, Y is a group of the formula: —O—, Alk is an ethylene group, Z is a group of the formula: —O—, R is a pyrimidinyl group being optionally substituted by a halogen atom or a lower alkoxy group, $R^1$ is an amino group being optionally substituted by 1 to 2 groups selected from a mono- or di-hydroxy-lower alkyl group, a lower alkyl group, an amino-lower alkyl group, a mono- or di-lower alkylamino-lower alkyl group, a lower alkoxy-lower alkyl group and a carboxy-lower alkyl group; a lower alkyl group substituted by a carboxyl group or a hydroxyl group; a lower alkoxy group being optionally substituted by a group selected from a hydroxyl group, a carboxyl group and a mono- or di-lower alkylamino group; a lower alkylthio group substituted by a group selected from a hydroxyl group, a carboxyl group, a lower alkoxycarbonyl group and a mono- or di-lower alkylamino group; a piperidyl group substituted by a hydroxyl group; or a tetrazolyl group.

Among these desired compounds [I], preferable compounds are compounds of the formula [I] wherein R is a pyrimidinyl group substituted by a halogen atom, and $R^1$ is a pyrimidinyl group, or compounds of the formula [I] wherein $R^1$ is an amino group being optionally substituted by a group selected from a hydroxy-lower alkyl group, a mono- or di-lower alkylamino-lower alkyl group and a lower alkoxy-lower alkyl group; an amino group substituted by a hydroxy-lower alkyl group or a lower alkyl group; a lower alkyl group being optionally substituted by a hydroxyl group; a lower alkoxy group being optionally substituted by a hydroxyl group or a carboxyl group; a lower alkylthio group substituted by a group selected from a hydroxyl group, a carboxyl group and a lower alkoxycarbonyl group; a piperidyl group substituted by a hydroxyl group; or a tetrazolyl group.

According to the present invention, the desired compounds [I] may be prepared by the following Process A, B, C, D, E, F or G.

Process A

The desired compounds [I] of the present invention may be prepared by reacting a compound of the formula [II]:

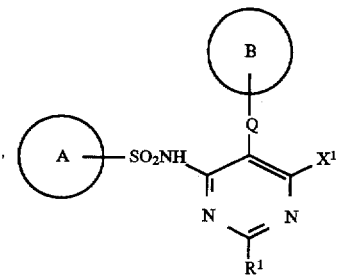

[II]

wherein $X^1$ is a reactive residue, and the other symbols are the same as defined above, with a compound of the formula [III]:

H—Y-Alk-Z—R  [III]

wherein the symbols are the same as defined above, or a salt thereof.

Process B

The compounds [I] may also be prepared by reacting a compound of the formula [IV]:

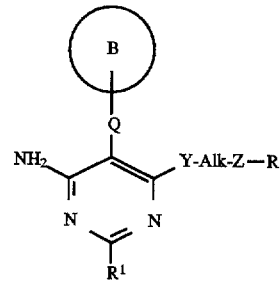

[IV]

wherein the symbols are the same as defined above, or a salt thereof, with a compound of the formula [V]:

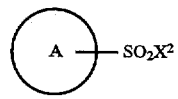

[V]

wherein $X^2$ is a reactive residue, and Ring A is the same as defined above.

Process C

The compounds [I] may also be prepared by reacting a compound of the formula [VI]:

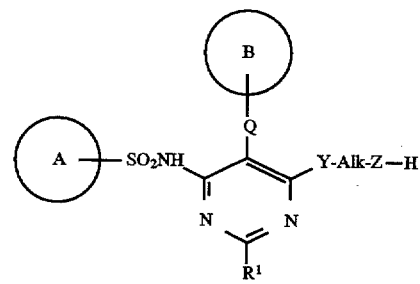

[VI]

wherein the symbols are the same as defined above, or a salt thereof, with a compound of the formula [VII]:

$X^3$—R  [VII]

wherein $X^3$ is a reactive residue and the other symbol is the same as defined above.

Process D

Among the desired compounds [I] of the present invention, the compound of the formula [I] wherein Q is a single bond, i.e. the compound of the formula [I-a]:

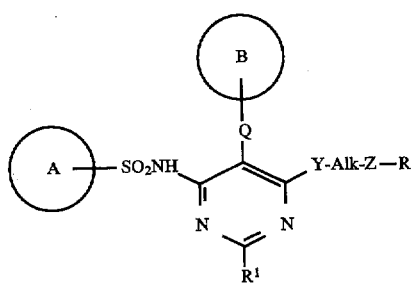

[I-a]

wherein the symbols are the same as defined above, may be prepared by reacting a compound of the formula [VIII]:

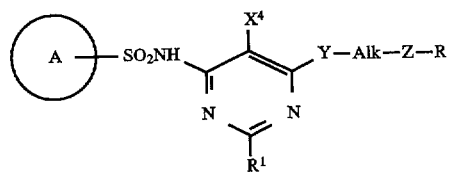

[VIII]

wherein $X^4$ is a reactive residue and the other symbols are the same as defined above, or a salt thereof, with a compound of the formula [IX]:

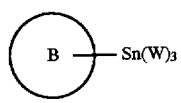

[IX]

wherein W is a lower alkyl group and Ring B is the same as defined above.

Process E

The compounds [I] may also be prepared by reacting a compound of the formula [II-A]:

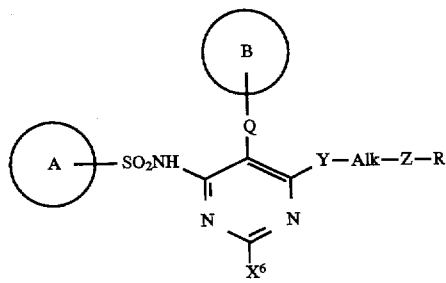

[II-A]

wherein $X^6$ is a lower alkylsulfonyl group or a phenylsulfonyl group, and the other symbols are the same as defined above, or a salt thereof, with a compound of the formula [III-A]:

$R^1$—H  [III-A]

wherein $R^1$ is the same as defined above, or a salt thereof.

Process F

Among the desired compounds [I] of the present invention, the compound of the formula [I] wherein $R^1$ is an amino group, i.e. the compound of the formula [I-c]:

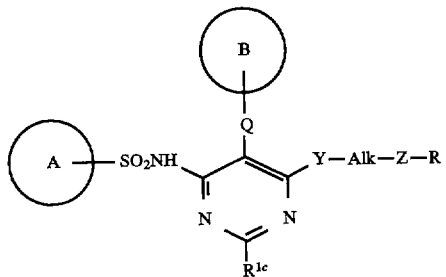

[I-c]

wherein $R^{1c}$ is an amino group, and the other symbols are the same as defined above, may be prepared by reducing a compound of the formula [I-b]:

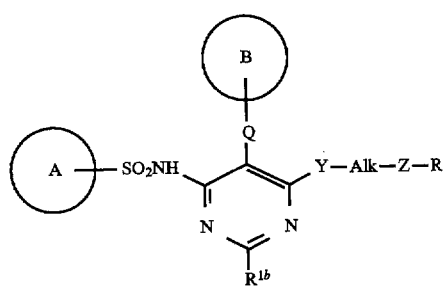

[I-b]

wherein $R^{1b}$ is an azide group, and the other symbols are the same as defined above, or a salt thereof.

Process G

Among the desired compounds [I] of the present invention, the compound of the formula [I] wherein $R^1$ is a substituted our unsubstituted thetrazolyl group, i.e. the compound of the formula [I-e]:

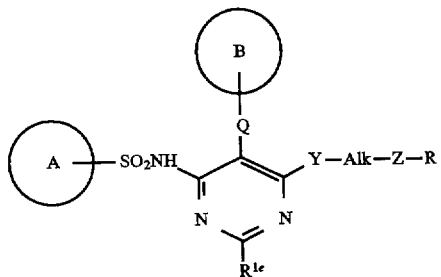

[I-e]

wherein $R^{1e}$ is a substituted or unsubstituted thetrazolyl group, and the other symbols are the same as defined above, may be prepared by reacting a compound of the formula [I-d]:

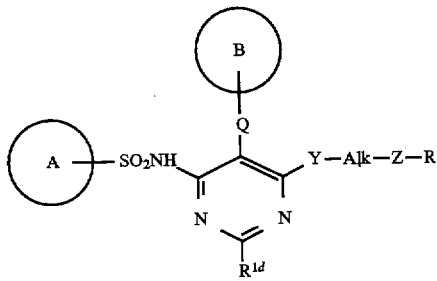

[I-d]

wherein $R^{1d}$ is a cyano group, and the other symbols are the same as defined above, or a salt thereof, with a tributyltin azide.

The salt of the compound [I-b], [I-d], [II], [II-A], [IV], [VI], or [VIII] are, for example, salts with an inorganic acid (e.g. hydrochloride, sulfate, etc.), and salts with an inorganic base (e.g. an alkali metal salt, an alkaline earth metal salt, etc.).

The reactive residues for $X^1$, $X^2$, $X^3$ and $X^4$ are preferably a halogen atom, a lower alkylsulfonyloxy group or an arylsulfonyloxy group, but a halogen atom is more preferable.

The above Processes are preferably carried out as follows.

Process A

The reaction of the compound [II] and the compound [III] or a salt thereof is carried out in the presence of an acid acceptor in a suitable solvent or without a solvent. The acid acceptor is preferably an alkali metal hydride, an alkali metal carbonate, an alkali metal amide, an alkali metal alkoxide, an alkyl-alkali metal, an alkali metal, an alkaline earth metal, an alkali metal hydroxide, an alkaline earth metal hydroxide, an organic base (e.g. 1,8-diazabicyclo [5.4.0]undeca-7-ene, etc.), and the like. The solvent includes, for example, dimethylsulfoxide, dimethylacetamide, dimethylformamide, hexamethylphosphoramide, sulfolane, 1,3-dimethyl-2-imidazolidinone, dioxane, tetrahydrofuran, toluene, ethylene glycol dimethyl ether, etc. The reaction is preferably carried out at temperatures of room temperature to 150° C., preferably at temperatures of room temperature to 120° C.

Process B

The reaction of the compound [IV] or a salt and the compound [V] is carried out in the presence of an acid acceptor in a suitable solvent or without a solvent. The acid acceptor and the solvent may be the same acid acceptors or the solvents for the above Process A. The reaction is preferably carried out at temperatures of 0° C. to 150° C., more preferably at temperatures of room temperature to 100° C. The reaction may preferably proceed in the presence of a catalytic amount of a phase transfer catalyst such as tetrabutylammonium hydrogen sulfate, trimethylbenzylammonium chloride, 18-crown-6, etc.

Process C

The reaction of the compound [VI] or a salt thereof and the compound [VII] is carried out in the presence of an acid acceptor in a suitable solvent or without a solvent. The acid acceptor may be the same acid acceptor for the above mentioned Process A. The solvent includes, for example, dimethylsulfoxide, dimethylacetamide, dimethylformamide, 1,3-dimethyl-2-imidazolidinone, ethylene glycol dimethyl ether, hexamethylphosphoramide, sulfolane, dioxane, tetrahydrofuran, toluene, or a mixture thereof. The reaction is preferably carried out at temperatures of room temperature to 150° C., more preferably at temperatures of room temperature to 100° C.

Process D

The reaction of the compound [VIII] or a salt thereof and the compound [IX] is carried out in the presence of a catalyst in a suitable solvent. The catalyst includes, for example, a palladium catalyst such as bis-(triphenylphosphine) palladium (II) chloride, palladium (II) acetate, tetrakis-(triphenylphosphine)palladium (0), and the like. The reaction may preferably proceed in the presence of a copper (I) salt such as copper (I) chloride, copper (I) bromide, copper (I) iodide, etc., according to the method disclosed in Journal of Organic Chemistry Vol. 58, p. 1963 (1993). The solvent includes, for example, dioxane, ethylene glycol dimethyl ether, dimethylacetamide, dimethylformamide, hexamethylphosphoramide, benzene, tetrahydrofuran, toluene, ethyl acetate, a lower alcohol, methylene chloride, chloroform, carbon tetrachloride, 1,3-dimethyl-2-imidazolidinone, diethyl ether, dimethoxyethane, water, or a mixture thereof. The reaction is preferably carried out at temperatures of 50° C. to 100° C.

Process E

The reaction of the compound [II-A] or a salt thereof and the compound [III-A] or a salt thereof is carried out in the presence or absence of an acid acceptor in a suitable solvent or without a solvent. The acid acceptor is preferably an alkali metal hydride, an alkali metal carbonate, an alkali metal alkoxide, an alkyl-alkali metal, an alkali metal, an alkaline earth metal, an alkali metal hydroxide, an alkaline earth metal hydroxide, an organic base (e.g. 1,8-diazabicyclo [5.4.0]undeca-7-ene, etc.), and the like. The solvent includes, for example, toluene, dimethylacetamide, dimethyl-formamide, dimethylsulfoxide, tetrahydrofuran, dimethoxymethane, etc. The reaction is preferably carried out at temperatures of room temperature to 150° C., preferably at temperatures of room temperature to 120° C.

Process F

The reduction reaction of the compound [I-b] or a salt thereof is carried out in the presence of a reducing agent in a suitable solvent or without a solvent. The reducing agent is preferably a phosphine compound such as triphenylphosphine, etc. The solvent includes, for example, tetrahydrofuran, dimethylformamide, water, etc., or a mixture thereof. The reaction is carried out at temperatures of 0° C. to 100° C., preferably at temperatures of room temperature to 60° C.

The compound [I-b] is prepared by reacting the compound [II-A] with sodium azide in a conventional manner.

Process G

The reaction of the compound [I-d] or a salt thereof and tributyltin azide is carried out in a suitable solvent or without a solvent. The solvent includes, for example, toluene, xylene, tetrahydrofuran, dimethylacetamide, dimethylformamide, etc., or a mixture thereof. The reaction is carried out at temperatures of room temperature to 150° C., preferably at temperatures of 50° C. to 120° C.

The compound [I-d] is prepared by reacting the compound [II-A] with potassium cyanide in a conventional manner.

The desired compounds [I] of the present invention can be converted each other to the other desired compound [I]. Such conversion of the present compounds [I] into the other compound [I] may be carried out in a different manner according to the kinds of the substituents thereof, and the conversion can be carried out according to the following Step (a) to (zz).

Step (a):

The desired compound [I] wherein R is a substituted aromatic heterocyclic or aryl group can be prepared by reacting the compound [I] wherein the corresponding R is a halogen-substituted aromatic heterocyclic or aryl group with a trialkyl-tin complex with a group to be a desired substituent in the presence of a catalyst. The catalyst may be any ones which are used in the above mentioned Process D. The reaction is preferably carried out at temperatures of room temperature to 100° C.

Step (b):

The desired compound [I] wherein R is a lower alkanoyl group (e.g. acetyl group, etc.)-substituted aromatic heterocyclic or aryl group can be prepared by acid-treatment of the compound [I] wherein the corresponding R is a lower alkoxy-lower alkenyl (e.g. 1-ethoxyvinyl group, etc.)-substituted aromatic heterocyclic or aryl group. The acid includes, for example, hydrochloric acid, sulfuric acid, p-toluenesulfonic acid, methanesulfonic acid, trifluoroacetic acid, acetic acid, etc. The reaction is preferably carried out at temperatures of 0° C. to room temperature.

Step (c):

The desired compound [I] wherein R is a hydroxy-substituted lower alkyl-substituted aromatic heterocyclic or aryl group can be prepared by treating the compound [I] wherein the corresponding R is a lower alkanoyl- or formyl-substituted aromatic heterocyclic or aryl group with a reducing agent. The reducing agent includes, for example, sodium borohydride, lithium borohydride, lithium aluminum hydride, diisobutyl aluminum hydride, etc. The reaction is preferably carried out at temperatures of 0° C. to room temperature.

Step (d):

The desired compound [I] wherein R is a lower alkyl-substituted aromatic heterocyclic or aryl group can be prepared by subjecting the compound [I] wherein the corresponding R is a hydroxy-substituted lower alkyl-substituted aromatic heterocyclic or aryl group to halogenation, followed by reduction of the product. The halogenation reaction is carried out by reacting the compound [I] with a halogenating agent such as thionyl chloride, phosphorus oxychloride, phosphorus pentachloride, phosphorus tribromide, etc. The reduction is carried out by using a palladium catalyst such as palladium-carbon, palladium-barium sulfate, palladium-aluminum oxide, palladium-black, etc., preferably in the presence of an acid acceptor under hydrogen atmosphere. The acid acceptor is preferably triethylamine, pyridine, potassium carbonate, sodium hydrogen carbonate, sodium acetate, etc. The reaction is preferably carried out at temperatures of room temperature to 60° C.

Step (e):

The desired compound [I] wherein R is an unsubstituted aromatic heterocyclic or aryl group can be prepared by reduction of the compound [I] wherein the corresponding R is a halogen-substituted aromatic heterocyclic or aryl group. The reduction is preferably carried out under the same conditions as those of the reduction in the above Step (d).

Step (f):

The desired compound [I] wherein R is an unsubstituted aromatic heterocyclic or aryl group can be prepared by subjecting the compound [I] wherein the corresponding R is a lower alkylthio-substituted aromatic heterocyclic or aryl group to desulfurization. The desulfurization reaction is preferably carried out in the presence of a catalyst such as Raney nickel, palladium-carbon, etc., at temperatures of room temperature to 50° C. under hydrogen atmosphere.

Step (g):

The desired compound [I] wherein R is an aromatic heterocyclic or aryl group substituted by a formyl group, a hydroxy-substituted lower alkyl group, or a hydroxy- and aryl-substituted lower alkyl group can be prepared by subjecting the compound [I] wherein the corresponding R is a halogen-substituted aromatic heterocyclic or aryl group to lithiation, followed by reacting the product with a corresponding carbonyl compound (e.g. dimethyl-formamide, acetone, benzaldehyde, etc.). The lithiation is preferably carried out by using a lithiating agent such as n-butyl lithium, s-butyl lithium, t-butyl lithium, etc. The reaction is carried out at temperatures of –100° C. to 25° C.

Step (h):

The desired compound [I] wherein R is an amino-substituted aromatic heterocyclic or aryl group can be prepared by reduction of the compound [I] wherein the corresponding R is a nitro-substituted aromatic heterocyclic or aryl group. The reduction is carried out in the presence of a transition metal catalyst under hydrogen atmosphere, or by reacting with a reducing agent. The transition metal catalyst includes, for example, palladium-carbon, palladium-aluminum oxide, palladium-black, colloidal palladium, platinum oxide, Raney nickel, etc., and the reducing agent includes, for example, lithium aluminum hydride, tin, stannous chloride, zinc, iron, etc. The reaction is preferably carried out at temperatures of –20° C. to 80° C.

Step (i):

The desired compound [I] wherein R is a lower alkanoylamino-substituted or arylcarbonylamino-substituted aromatic heterocyclic or aryl group can be prepared by acylating the compound [I] wherein the corresponding R is an amino-substituted aromatic heterocyclic or aryl group. The acylating agent includes, for example, a carboxylic acid or a reactive derivative thereof (e.g. an acid chloride, an acid bromide, an acid anhydride, a mixed acid anhydride, etc.). When a free carboxylic acid is used, the reaction is preferably carried out in the presence of a condensing agent such as N,N'-dicyclohexylcarbodiimide, N-dimethylaminopropyl-N'-ethylcarbodiimide, diethylphosphoric cyanide, diphenylphosphoric azide, etc. When a reactive derivative of carboxylic acid is used, the reaction is preferably carried out in the presence of an acid acceptor such as an alkali metal hydroxide, an alkali metal hydrogen carbonate, an alkali metal carbonate, an organic base (e.g. triethylamine, pyridine, etc.), etc. The reaction is preferably carried out at temperatures of –20° C. to 100° C.

Step (j):

The desired compound [I] wherein R is a mono- or di-lower alkyl-amino-substituted aromatic heterocyclic or aryl group can be prepared by subjecting the compound [I] wherein the corresponding R is an amino-substituted aromatic heterocyclic or aryl group to alkylation. The alkylation is carried out by (i) reacting in the presence of an acid acceptor with a lower alkyl halide (e.g. a lower alkyl chloride, a lower alkyl bromide, etc.) or a lower alkyl sulfonate (e.g. a lower alkyl methanesulfonate, a lower alkyl toluenesulfonate, etc.), etc., or by (ii) subjecting a reaction product with a lower alkyl aldehyde to reduction in the presence of a reducing agent. The acid acceptor includes, for example, an alkali metal hydroxide, an alkali metal hydrogen carbonate, an alkali metal carbonate, an organic base (e.g. triethylamine, pyridine, etc.), etc. The reducing agent includes, for example, sodium borohydride, sodium triacetoxyborohydride, formic acid, etc. The reaction is preferably carried out at temperatures of 0° C. to 100° C.

Step (k):

The desired compound [I] wherein R is a tetrazolyl-substituted aromatic heterocyclic or aryl group can be prepared by reacting the compound [I] wherein the corresponding R is a cyano-substituted aromatic heterocyclic or aryl group with tributyltin azide. The reaction is preferably carried out at temperatures of 50° C. to 120° C.

Step (l):

The desired compound [I] wherein R is a protected or unprotected carboxyl-substituted lower alkoxy-substituted aromatic heterocyclic or aryl group can be prepared by reacting the compound [I] wherein the corresponding R is a hydroxy-substituted aromatic heterocyclic or aryl group with a protected or unprotected carboxyl-substituted lower alkyl halide or a protected or unprotected carboxyl-substituted lower alkyl sulfonate, etc. The reaction is preferably carried out in the presence of an acid acceptor such as an alkali metal hydroxide, an alkali metal hydrogen carbonate, an alkali metal carbonate, an organic base (e.g. triethylamine, pyridine, etc.). The reaction is preferably carried out at temperatures of 0° C. to 100° C. The protecting group of carboxyl group may be any conventional protecting groups of carboxyl group, and the protecting group can be removed by a conventional method which is selected according to the kind of the protecting group to be removed.

Step (m):

The desired compound [I] wherein R is a lower alkoxy-lower alkyl-substituted aromatic heterocyclic or aryl group can be prepared by halogenating the compound [I] wherein the corresponding R is a hydroxy-substituted lower alkyl-substituted aromatic heterocyclic or aryl group, followed by alkoxylating the product. The halogenating agent may be any halogenating agents used in the Step (d). The reaction is preferably carried out at temperatures of −20° C. to 100° C. The alkoxylation reaction is carried out by reacting the product with a lower alcohol such as methanol, ethanol, isopropanol, etc. The alkoxylation reaction is preferably carried out in the presence of an acid acceptor, and the acid acceptor includes, for example, an alkali metal hydroxide, an alkali metal hydrogen carbonate, an alkali metal carbonate, an organic base (e.g. triethylamine, pyridine, etc.). The reaction is preferably carried out at temperatures of −20° C. to 100° C.

Step (n):

The desired compound [I] wherein R is a lower alkylsufinyl- and/or a lower alkyl sulfonyl-substituted aromatic heterocyclic or aryl group can be prepared by oxidizing the compound [I] wherein the corresponding R is a lower alkylthio-substituted aromatic heterocyclic or aryl group with an oxidizing agent. The oxidizing agent is preferably 3-chloroperbenzoic acid, peracetic acid, hydrogen peroxide, pertrifluoroacetic acid, sodium periodate, sodium hypochlorite, potassium permanganate, and the like. The reaction is carried out at temperatures of 0° C. to 50° C.

Step (o):

The desired compound [I] wherein R is a lower alkylthio-substituted aromatic heterocyclic or aryl group can be prepared by reacting the compound [I] wherein the corresponding R is a lower alkylsufinyl-substituted aromatic heterocyclic or aryl group with an acid anhydride, subjecting the product to hydrolysis or alcoholysis to give a thiol compound, followed by alkylating the thiol compound with a lower alkyl halide in the presence of a base. The acid anhydride is preferably trifluoroacetic anhydride, acetic anhydride, etc. The base is preferably potassium carbonate, sodium carbonate, a sodium lower alkoxide (e.g. sodium methoxide, sodium ethoxide, etc.), etc. The reaction is preferably carried out at temperatures of 0° C. to 50° C.

Step (p):

The desired compound [I] wherein R is a cyano-substituted aromatic heterocyclic or aryl group can be prepared by reacting the compound wherein the corresponding R is a halogen-substituted aromatic heterocyclic or aryl group with zinc cyanide in the presence of a catalyst. The catalyst is preferably the same catalyst as that in the above Process D. The reaction is preferably carried out at temperatures of 60° C. to 100° C.

Step (q):

The desired compound [I] wherein R is a trimethylsilyl-substituted lower alkynyl- or a hydroxy-substituted lower alkynyl-substituted aromatic heterocyclic or aryl group can be prepared by subjecting the compound [I] wherein the corresponding R is a halogen-substituted aromatic heterocyclic or aryl group to trimethylsilyl-substituted lower alkynylation, or to hydroxy-substituted lower alkynylation. The trimethylsilyl-substituted lower alkynylation, or the hydroxy-substituted lower alkynylation is carried out in the presence of a catalyst and an organic base. The catalyst is preferably the same catalyst as that in the above Process D, and the organic base is preferably the same organic base as that in the above Step (j). The reaction can preferably proceed in the presence of a copper (I) salt like the above Process D. The reactions is carried out at temperatures of room temperature to 100° C.

Step (r):

The desired compound [I] wherein R is a lower alkynyl-substituted aromatic heterocyclic or aryl group can be prepared by hydrolyzing the compound [I] wherein the corresponding R is a trimethylsilyl-substituted lower alkynyl-substituted aromatic heterocyclic or aryl group in the presence of an acid or an inorganic base. The acid includes, for example, hydrochloric acid, sulfuric acid, hydrobromic acid, etc., and the base includes, for example, potassium carbonate, sodium carbonate, potassium hydroxide, sodium hydroxide, etc. The reaction is preferably carried out at temperatures of 0° C. to room temperature.

Step (s):

The desired compound [I] wherein R is a phenyl-lower alkyl-substituted aromatic heterocyclic or aryl group can be prepared by reducing the compound [I] wherein the corresponding R is a phenylalkenyl-substituted aromatic heterocyclic or aryl group under hydrogen atmosphere in the presence of a catalyst. The catalyst may be the same catalyst as that in the above Step (d). The reaction is preferably carried out at temperatures of room temperature to 60° C.

Step (t):

The desired compound [I] wherein Ring A and/or Ring B are a formyl-substituted hydrocarbon group or heterocyclic group can be prepared by hydrolyzing the compound [I] wherein the corresponding Ring A and/or Ring B are a hydrocarbon group or heterocyclic group substituted by a di-lower alkoxy-substituted lower alkyl group in the presence of an acid. The acid includes, for example, an organic acid such as p-toluenesulfonic acid, oxalic acid, etc., and an inorganic acid such as hydrochloric acid, sulfuric acid, hydrobromic acid, etc. The reaction is preferably carried out at temperatures of 0° C. to 50° C.

Step (u):

The desired compound [I] wherein Ring A and/or Ring B are a hydrocarbon group or heterocyclic group substituted by a lower alkoxycarbonyl-lower alkenyl group can be prepared by reacting the compound wherein the corresponding Ring A and/or Ring B are a hydrocarbon group or heterocyclic group substituted by formyl group with a triphenylphosphorane complex with a group to be a desired substituent. The reaction is preferably carried out at temperatures of room temperature for 60° C.

Step (v):

The desired compound [I] wherein Ring A and/or Ring B are a hydrocarbon group or heterocyclic group substituted by a carboxy-substituted lower alkenyl group can be prepared by hydrolyzing the compound [I] wherein the corresponding Ring A and/or Ring B are a hydrocarbon group or heterocyclic group substituted by a lower alkoxycarbonyl-lower alkenyl group in the presence of an inorganic base. The inorganic base includes, for example, sodium hydroxide, etc. The reaction is carried out at temperatures of 0° C. to room temperature.

Step (w):

The desired compound [I] wherein Q is a group of the formula: —SO— or —SO$_2$— can be prepared by oxidizing the compound [I] wherein the corresponding Q is a group of the formula: —S— with an oxidizing agent. The oxidizing agent includes, for example, 3-chloroperbenzoic acid, peracetic acid, hydrogen peroxide, pertrifluoroacetic acid, sodium periodate, sodium hypochlorite, potassium permanganate, etc. The reaction is preferably carried out at temperatures of 0° C. to 50° C.

Step (x):

The desired compound [I] wherein $R^1$ is a carboxy-lower alkylthio group can be prepared by subjecting the compound [I] wherein the corresponding $R^1$ is a lower alkoxycarbonyl-lower alkylthio group in the presence of bistributyltin oxide to hydrolysis. The reaction is preferably carried out at temperatures of 60° C. to 120° C.

Step (y):

The desired compound [I] wherein $R^1$ is a hydroxy-substituted lower alkoxy group can be prepared by reacting the compound [I] wherein the corresponding $R^1$ is a protected hydroxy (e.g. 2-tert-butyldiphenylsilyloxy, etc.)-substituted lower alkoxy group in the presence of de-protecting agent. The de-protecting agent is preferably tetrabutylammonium fluoride, hydrogen fluoride-pyridine, etc. The reaction is preferably carried out at temperatures of 0° C. to room temperature.

Step (z):

The desired compound [I] wherein $R^1$ is a hydroxy-substituted lower alkyl group can be prepared by treating the compound [I] wherein the corresponding $R^1$ is a protected hydroxy (e.g. methoxymethyloxyp, etc.)-substituted lower alkyl group with an acid. The acid is preferably trifluoroacetic acid, p-toluenesulfonic acid, methanesulfonic acid, sulfuric acid, hydrochloric acid, etc. The reaction is preferably carried out at temperatures of 0° C. to room temperature.

Step (zz):

The desired compound [I] wherein $R^1$ is a hydroxy-lower alkyl-substituted amino group can be prepared by treating the compound [I] wherein the corresponding $R^1$ is a protected hydroxy-lower alkyl (e.g. tetrahydropyranyloxy-lower alkyl group, etc.)-substituted amino group with an acid. The acid is preferably hydrochloric acid, sulfuric acid, p-toluenesulfonic acid, methanesulfonic acid, trifluoroacetic acid, etc. The reaction is preferably carried out at temperatures of 0° C. to room temperature.

The solvent used for the reactions of Steps (a) to (zz) may be any one which does not disturb the reaction, for example, dioxane, ethylene glycol dimethyl ether, dimethylacetamide, dimethylformamide, hexamethylphosphoramide, benzene, tetrahydrofuran, toluene, ethyl acetate, a lower alcohol, methylene chloride, chloroform, carbon tetrachloride, 1,3-dimethyl-2-imidazolidinone, diethyl ether, dimethoxyethane, dimethylsulfoxide, water, or a mixture thereof.

The compounds [II] and [VI] of the present invention may be prepared according to the method disclosed in Japanese Patent First Publication (Kokai) No. 155864/1993 or Japanese Patent First Publication (Kokai) No. 222003/1993. That is, the compound [II] wherein Q is a single bond may be prepared as follows. A compound of the formula [X]:

[X]

wherein Ring B is the same as defined above, is treated with a halogenating agent (e.g. thionyl chloride, etc.), treating the resulting corresponding acid halide with an ethanol, followed by reacting the resulting ester with diethyl carbonate in the presence of a base (e.g. sodium hydride, potassium t-butoxide, etc.) to give a compound of the formula [XI]:

[XI]

wherein Ring B is the same as defined above. Further, the compound [XI] is treated with ammonia to give an amide of the formula:

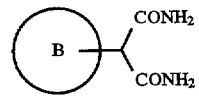

wherein Ring B is the same as defined above, followed by reacting the amide with a compound of the formula:

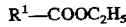

$R^1$—COOC$_2$H$_5$ wherein $R^1$ is the same as defined above, in the presence of a base (e.g. sodium ethylate, etc.) to give a compound of the formula [XII]:

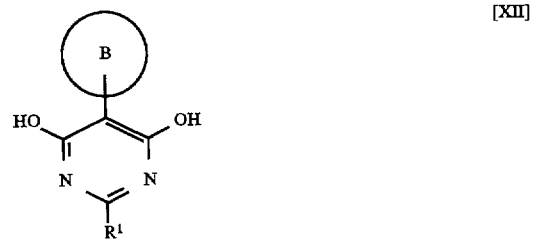

[XII]

wherein the symbols are the same as defined above, or the compound [XI] is reacted with an amidine of the formula [XIII]:

[XIII]

wherein $R^1$ is the same as defined above, in the presence of a base (e.g. sodium methoxide, etc.) to give the compound [XII]. Further, the hydroxyl groups of the compound [XII] are converted into a reactive residue by treating with a halogenating agent (e.g. phosphorus oxychloride, etc.) to give a compound of the formula [XIV]:

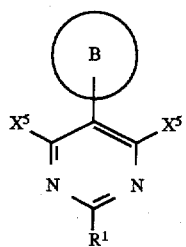
[XIV]

wherein $R^5$ is a reactive residue and the other symbols are the same as defined above, or the compound [XI] is reacted with urea in the presence of a base (e.g. sodium methoxide, etc.) to give a compound of the formula:

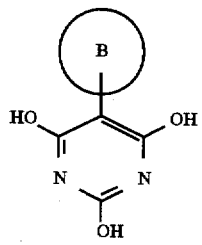

wherein Ring B is the same as defined above, and the hydroxyl groups of the compound are converted into a reactive residue by treating with a halogenating agent (e.g. phosphorus oxychloride, etc.) to give a compound of the formula [XV]:

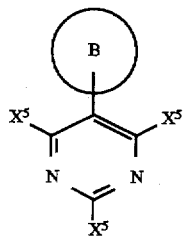
[XV]

wherein the symbols are the same as defined above. Further, the compound of the formula [XV] is reacted with a compound of the formula [XVI]:

$R^1\text{-}W^1$
[XVI]

wherein $W^1$ is a leaving group, and $R^1$ is the same as defined above to give the compound of the formula [XIV], which is reacted with a compound of the formula [XVII]:

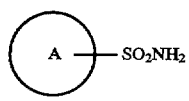
[XVII]

wherein Ring A is the same as defined above, in the presence of an acid acceptor (e.g. sodium hydroxide, potassium hydroxide, potassium carbonate, sodium hydride, etc.) to give the compound [II] wherein Q is a single bond.

On the other hand, the compound [II] wherein Q is a group of the formula: —O— may be prepared as follows. A compound of the formula [XVIII]:

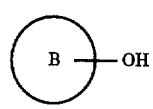
[XVIII]

wherein Ring B is the same as defined above, is reacted with bromomalonic acid diethyl ester in the presence of an acid acceptor (e.g. potassium carbonate, etc.) to give a compound of the formula [XIX]:

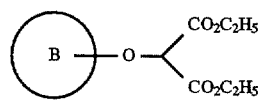
[XIX]

wherein Ring B is the same as defined above, followed by reacting the compound [XIX] with the amidine [XIII] in the presence of a base (e.g. sodium methoxide, etc.) to give a compound of the formula [XX]:

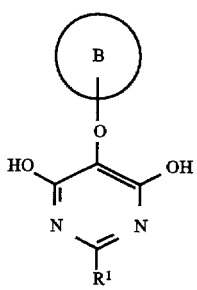
[XX]

wherein the symbols are the same as defined above. Further the compound [XX] is reacted in the same manner as the conversion reaction of the hydroxyl groups of the compound [XII] into the reactive residues wherein Q is a single bond, to give a compound of the formula [XXI]:

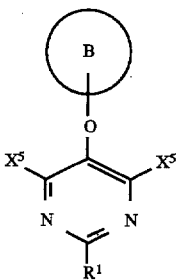
[XXI]

wherein the symbols are the same as defined above, or by reacting the compound [XIX] with urea in the presence of a base (e.g. sodium methoxide, etc.) to give a compound of the formula:

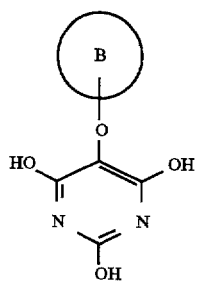

wherein Ring B is the same as defined above, converting the hydroxyl groups of the above compound into a reactive residue by treating with a halogenating agent (e.g. phosphorus oxychloride, etc.), reacting the resulting compound of the formula [XXII]:

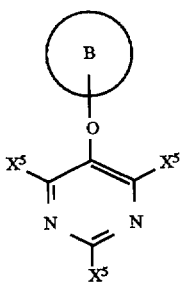

[XXII]

wherein the symbols are the same as defined above, with the compound [XVI], followed by treating the resulting compound [XXI] under the same conditions as those in the reaction of the compound [XIV] and the compound [XVII] to give the compound [II] wherein Q is a group of the formula: —O—.

Moreover, the compound [VI] may be prepared by reacting the corresponding compound [II] with a compound of the formula [XXIII]:

H—Y-Alk-Z—H    [XXIII]

wherein Y, Alk and Z are the same as defined above, in the presence of an acid acceptor (e.g. sodium hydride, etc.).

The starting compound [IV] of the present invention may be prepared, for example, by (i) reacting the compound [XIV] or the compound [XXI] with the compound [III] in the presence of an acid acceptor (e.g. sodium hydride, etc.) to give a compound [XXIV]:

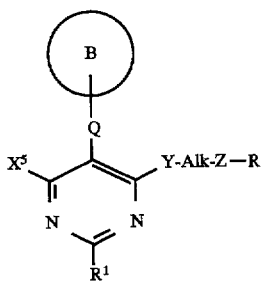

[XXIV]

wherein the symbols are the same as defined above, reacting the product with sodium azide to give a compound of the formula [XXV]:

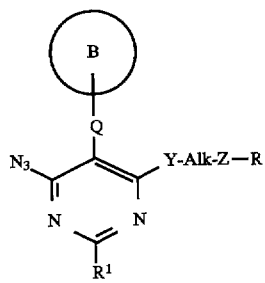

[XXV]

wherein the symbols are the same as defined above, followed by subjecting the product to catalytic hydrogenation, or by (ii) reacting the compound [XIV] or the compound [XXI] with ammonia to give a compound of the formula [XXVI]:

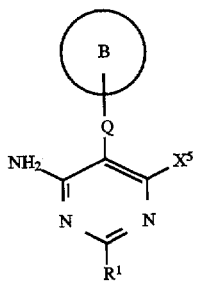

[XXVI]

wherein the symbols are the same as defined above, followed by reacting the product with the compound [III] in the presence of an acid acceptor (e.g. sodium hydride, etc.).

The compounds [IV] may also be prepared by (i) reacting the compound [XIV] or the compound [XXI] with the compound [XXIII] in the presence of an acid acceptor (e.g. sodium hydride, etc.) to give a compound [XXVII]:

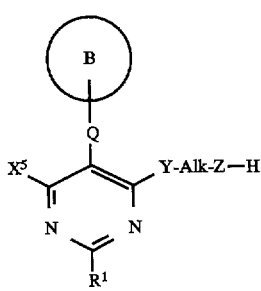

[XXVII]

wherein the symbols are the same as defined above, reacting the product with sodium azide to give a compound of the formula [XXVIII]:

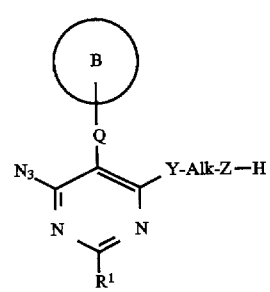

[XXVIII]

wherein the symbols are the same as defined above, subjecting the product to catalytic hydrogenation to give a compound [XXIX]:

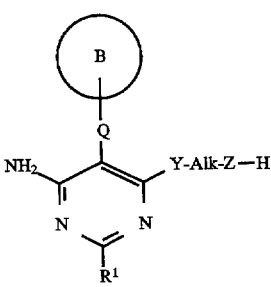

[XXIX]

wherein the symbols are the same as defined above, followed by reacting the product with the compound [VII] in the presence of an acid acceptor (e.g. sodium hydride, etc.), or by (ii) reacting the compound [XXVI] with the compound [XXIII] to give the compound [XXIX], followed by reacting the product with the compound [VII] in the presence of an acid acceptor (e.g. sodium hydride, etc.).

Moreover, the compound [VIII] may be prepared by (i) reacting a compound of the formula [XXX]:

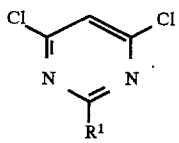  [XXX]

wherein $R^1$ is the same as defined above, with the compound [XVII] in the presence of an acid acceptor (e.g. sodium hydride, etc.) to give a compound of the formula [XXXI]:

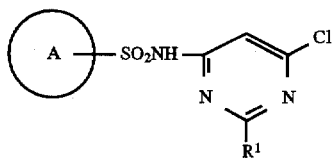  [XXXI]

wherein the symbols are the same as defined above, reacting the product with the compound [III] in the presence of an acid acceptor (e.g. sodium hydride, etc.) to give a compound of the formula [XXXII]:

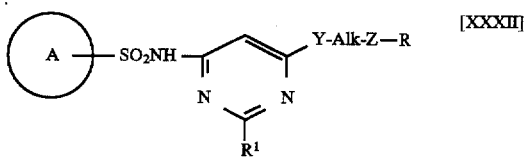  [XXXII]

wherein the symbols are the same as defined above, followed by the introduction of the reactive residue, $X^4$, to give the compound [VIII] by treating the compound [XXXII] with a halogenating agent, or by (ii) reacting the compound [XXX] with the compound [III] in the presence of an acid acceptor (e.g. sodium hydride, etc.) to give a compound of the formula [XXXIII]:

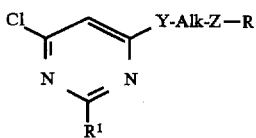  [XXXIII]

wherein the symbols are the same as defined above, reacting the compound [XXXIII] with sodium azide to give a compound of the formula [XXXIV]:

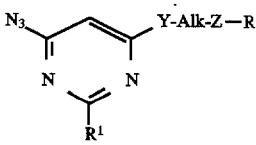  [XXXIV]

wherein the symbols are the same as defined above, subjecting the compound [XXXIV] to catalytic hydrogenation to give a compound [XXXV]:

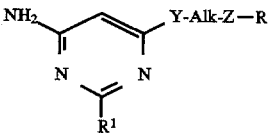  [XXXV]

wherein the symbols are the same as defined above, reacting the compound [XXXV] with the compound [V] in the presence of an acid acceptor (e.g. sodium hydride, etc.) to give the compound [XXXII], followed by the introduction of the reactive residue, $X^4$, to give the compound [VIII] by treating with a halogenating agent.

The compounds [VIII] may be prepared by (i) reacting the compound [XXXI] with the compound [XXIII] in the presence of an acid acceptor (e.g. sodium hydride, etc.) to give a compound of the formula [XXXVI]:

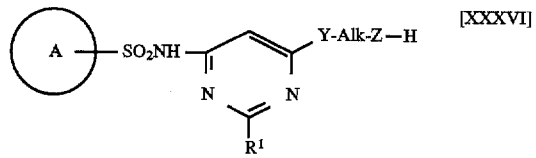  [XXXVI]

wherein the symbols are the same as defined above, followed by treating the compound [XXXVI] with a halogenating agent (e.g. N-bromosuccinimide, bromine, etc.) to introduce the reactive residue, $X^4$, to give a compound of the formula [XXXVII]:

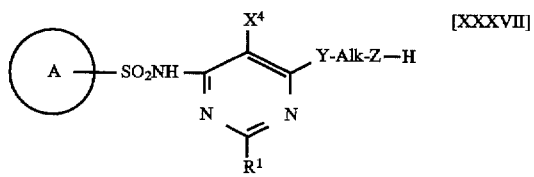  [XXXVII]

wherein the symbols are the same as defined above, followed by reacting the compound [XXXVII] with the compound [VII] in the presence of an acid acceptor (e.g. sodium hydride, etc.), or by (ii) reacting the compound [XXX] with the compound [XXIII] in the presence of an acid acceptor (e.g. sodium hydride, etc.) to give a compound of the formula [XXXVIII]:

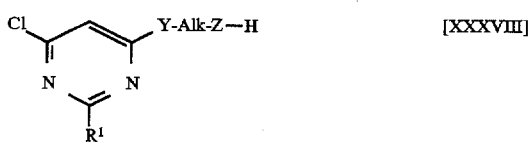  [XXXVIII]

wherein the symbols are the same as defined above, reacting the compound [XXXVIII] with sodium azide to give a compound of the formula [XXXIX]:

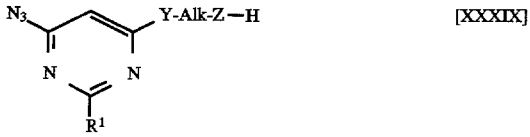  [XXXIX]

wherein the symbols are the same as defined above, followed by subjecting the compound [XXXIX] to catalytic hydrogenation to give a compound of the formula [XXXX]:

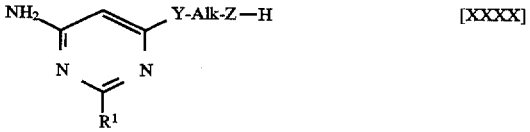  [XXXX]

wherein the symbols are the same as defined above, reacting the compound [XXXX] with the compound [V] to give a compound of the formula [XXXVI], treating the compound [XXXVI] with a halogenating agent (e.g. N-bromosuccinimide, bromine, etc.) to introduce a reactive residue to give the compound [XXXVII], followed by reacting the compound [XXXVII] with the compound [VII] in the presence of an acid acceptor (e.g. sodium hydride, etc.).

The compound [II-A] may be prepared, for example, by the method disclosed in Japanese Patent Second Publication (Kokoku) No. 7054/1977. That is, the compound [II-A] wherein $X^6$ is a methylsulfonyl group may be prepared by reacting a compound of the formula [VI-A]:

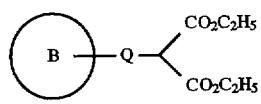

[VI-A]

wherein Ring B and Q are the same as defined above, with thiourea in the presence of an alkali metal alkoxide (e.g. sodium methoxide, etc.), an alkali metal hydroxide, an alkali metal carbonate, etc., reacting the product with methyl iodide to give a compound of the formula [VII-A]:

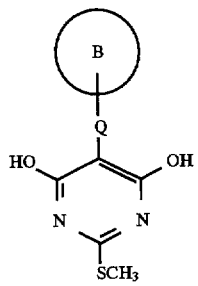

[VII-A]

wherein Ring B and Q are the same as defined above, then converting the hydroxyl groups of the compound [VII-A] into a reactive residue by treating the compound [VII-A] with a halogenating agent (e.g. phosphorus oxychloride, etc.) to give a compound of the formula [VIII-A]:

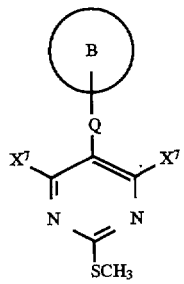

[VIII-A]

wherein $X^7$ is a reactive residue and the other symbols are the same as defined above, which is further reacted with a compound of the formula [IX-A]:

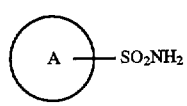

[IX-A]

wherein Ring A is the same as defined above, in the presence of an acid acceptor (e.g. sodium hydride, sodium hydroxide, potassium hydroxide, potassium carbonate, etc.) to give a compound of the formula [X-A]:

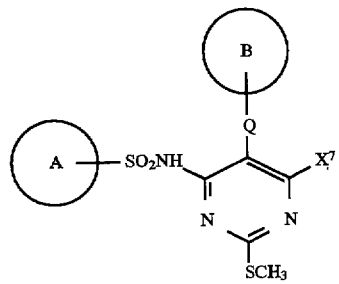

[X-A]

wherein the symbols are the same as defined above, reacting the compound [X-A] with the compound [XXIII] in the presence of an acid acceptor (e.g. sodium hydride, an alkali metal alkoxide, an alkali metal, etc.) to give a compound of the formula [XI-A]:

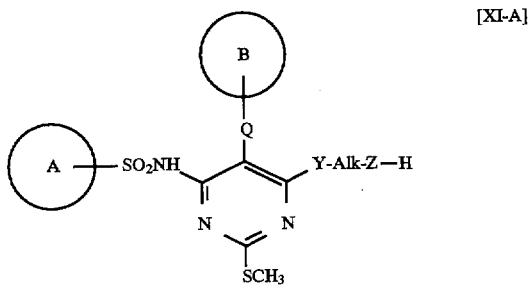

[XI-A]

wherein the symbols are the same as defined above, reacting the compound [XI-A] with the compound [VII] in the presence of an acid acceptor (e.g. sodium hydride, an alkali metal alkoxide, an alkali metal, etc.) to give a compound of the formula [XII-A]:

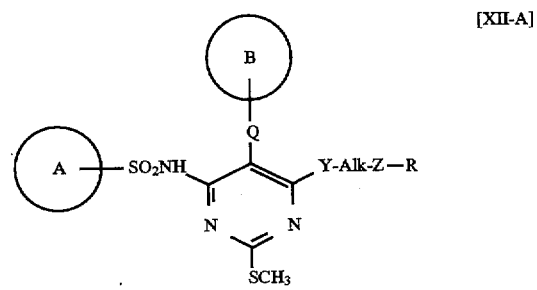

[XII-A]

wherein the symbols are the same as defined above, then followed by treating the compound [XII-A] with an oxidizing agent (e.g. m-chloroperbenzoic acid, etc.).

On the other hand, the compound [VI] wherein $R^1$ is a methylsulfonyl group may be prepared by treating the compound [XI-A] with an oxidizing agent (e.g. m-chloroperbenzoic acid, etc.) to give a compound of the formula [XIII-A]:

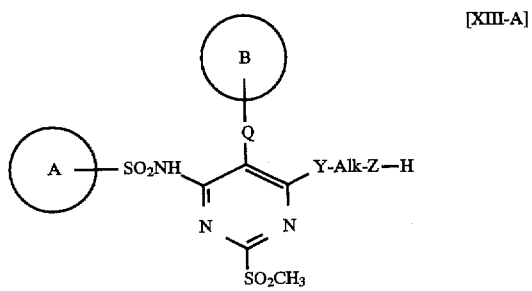

[XIII-A]

wherein the symbols are the same as defined above, protecting the hydroxyl group, —Z—H, of the compound

[XIII-A] by a protecting group such as tetrahydropyranyl, etc., reacting the product with the compound [III-A] in the presence or absence of an acid acceptor (e.g. sodium hydride, sodium hydroxide, potassium hydroxide, potassium carbonate, etc.), followed by removing the protecting group from the product.

The desired compounds [I] of the present invention may exist in the form of an optical isomer based on an asymmetric carbon atom or an asymmetric sulfur atom thereof, and the present invention also includes these optical isomers and a mixture thereof.

The desired compounds [I] of the present invention may be clinically used either in the form of a free form or in the form of a pharmaceutically acceptable salt thereof. The pharmaceutically acceptable salt includes an acid-addition salt with an inorganic acid or organic acid, salts with an inorganic base, organic base or amino acid, for example, hydrochloride, sulfate, hydrobromide, methanesulfonate, acetate, fumarate, maleate, oxalate, an alkali metal salt (e.g. sodium, potassium, etc.), an alkaline earth metal salt (e.g. magnesium, calcium, etc.), triethylamine salt, a salt with lysine, and the like.

The desired compounds [I] of the present invention or a pharmaceutically acceptable salt thereof may be administered either orally or parenterally in the form of a conventional pharmaceutical preparation such as tablets, granules, capsules, powders, injections, inhalants, etc., which is prepared by a conventional method.

The dosage of the desired compounds [I] of the present invention and a pharmaceutically acceptable salt thereof may vary according to the administration route, ages, weights and conditions of the patients, but it is usually in the range of about 0.001 to 100 mg/kg/a day.

Throughout the present specification and claims, the lower alkyl group, the lower alkoxy group, the lower alkylene group, the lower alkylenedioxy group, the lower alkythio group, the lower alkylamino group, the lower alkylsulfinyl group and the lower alkylsulfonyl group mean ones having 1 to 6 carbon atoms, especially ones having 1 to 4 carbon atoms, respectively. The lower alkenyl group, the lower alkanoyl group, the lower alkanoylamino group, the lower alkoxycarbonyl group, the lower alkynyl group, the lower alkenyloxy group, the lower alkenylene group, the N-lower alkylcarbamoyloxy group, the N-lower alkoxyiminomethyl group and the N-lower alkylamino-carbonyl group mean ones having 2 to 7 carbon atoms, especially ones having 2 to 5 carbon atoms, respectively. The cycloalkyl group means ones having 3 to 8 carbon atoms, especially having 3 to 6 carbon atoms. The halogen atom is chlorine, bromine, fluorine, or iodine.

The present invention is illustrated in more detail by the following Examples and Reference Examples, but should not be construed to be limited thereto.

EXAMPLE 1

N-[6-{2-(5-Bromopyrimidin-2-yloxy)ethoxy}-5-(2-thienyl)-2-(2-pyrimidinyl)-pyrimidin-4-yl]-4-tert-butylbenzenesulfonamide:

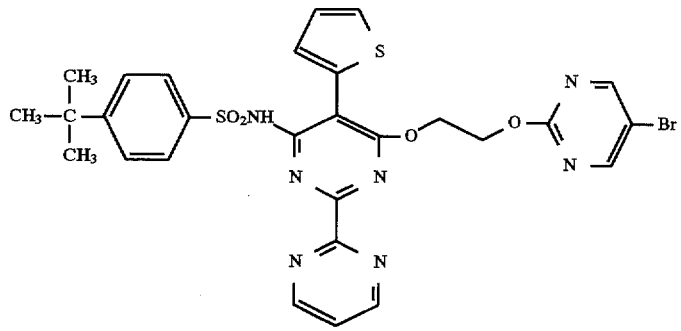

To a solution of 4-tert-butyl-N-{6-(2-hydroxyethoxy)-5-(2-thienyl)-2-(2-pyrimidinyl)-pyrimidin-4-yl}benzenesulfonamide (1790 mg) in tetrahydrofuran (20 ml) is added sodium hydride (60% dispersion, 413 mg) at room temperature, and thereto is added dimethylacetamide (4 ml), and the mixture is stirred for 20 minutes. To the reaction mixture is added 5-bromo-2-chloro-pyrimidine (952 mg), and the mixture is stirred at room temperature for 46 hours. The mixture is acidified with 10% hydrochloric acid, and extracted with ethyl acetate. The ethyl acetate layer is washed, dried, and evaporated under reduced pressure to remove the solvent. The residue is purified by silica gel column chromatography (solvent; chloroform:methanol= 4:1) to give the title compound (617 mg) as a crystal.

M.p. 222.5°–223.5° C.

IR (nujol, cm$^{-1}$): 1640, 1610

MS (m/z): 670 (MH$^{+}$)

EXAMPLE 2

N-{6-[2-(5-Bromopyrimidin-2-yloxy)ethoxy]-5-(4-methylphenyl)-pyrimidin-4-yl}naphthalenesulfonamide:

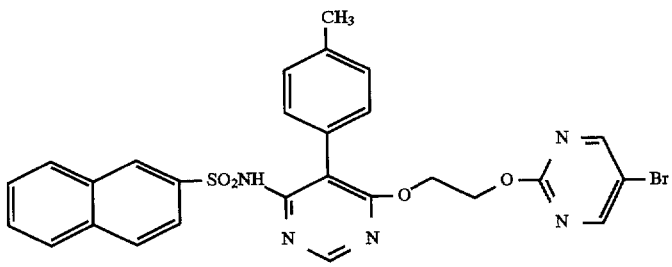

A mixture of 4-amino-6-[2-(5-bromopyrimidin-2-yloxy)ethoxy]-5-(4-methylphenyl)pyrimidine (150 mg), 2-naphthalenesulfonyl chloride (170 mg), 96% potassium hydroxide (powder, 300 mg), tetrabutylammonium hydrogen sulfate (34 mg) and toluene (10 ml) is stirred at room temperature overnight. The mixture is diluted with a saturated aqueous ammonium chloride solution, and extracted with ethyl acetate. The ethyl acetate layer is washed, dried, and evaporated under reduced pressure to remove the solvent. The residue is purified by silica gel column chromatography (solvent; chloroform:ethyl acetate=8:1), and recrystallized from hexaneotetrahydrofuran to give the title compound (187 mg).

M.p. 204.0°–204.5° C.

IR (nujol, cm$^{-1}$): 1570

MS (m/z): 594 (MH$^+$)

EXAMPLES 3–6

4-Amino-6-[2-(5-bromopyrimidin-2-yloxy)ethoxy]-5-(4-methylphenyl)-pyrimidine and the corresponding starting compounds are treated in the same manner as in Example 2 to give the compounds as listed in Table 1.

TABLE 1

| Ex. No. | Ring A | Physical properties |
|---|---|---|
| 3 | 1-naphthyl | M.p. 169.5–170.5° C. |
| 4 | 5-(dimethylamino)-1-naphthyl | M.p. 170.5–172.0° C. |
| 5 | 2-thienyl | M.p. 152–155° C. |
| 6 | 5-(2-pyridyl)-2-thienyl | M.p. 226–227° C. |

EXAMPLE 7

N-{6-[2-(5-Bromopyrimidin-2-yloxy)ethoxy]-5-(2-methoxyphenoxy)-2-(2-pyrimidinyl)pyrimidin-4-yl}-2-thiophenesulfonamide:

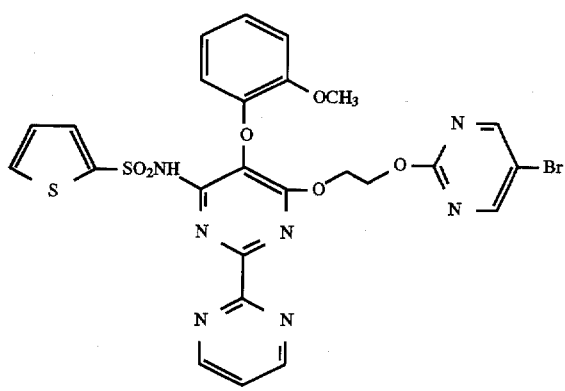

A mixture of 4-amino-6-[2-(5-bromopyrimidin-2-yloxy)ethoxy]-5-(2-methoxyphenoxy)-2-(2-pyrimidinyl)-pyrimidine (100 mg), sodium hydride (60 dispersion, 53.5 mg) and tetrahydrofuran (3 ml) is stirred at room temperature for 20 minutes. To the mixture is added thiophenesulfonyl chloride (23.4 mg), and the mixture is stirred for 22 hours. The reaction solution is treated with a saturated aqueous ammonium chloride solution, and extracted with ethyl acetate. The ethyl acetate layer is washed, dried, and evaporated under reduced pressure to remove the solvent. The residue is purified by preparative thin layer chromatography (solvent; chloroform: methanol=10:1) to give the title compound (49.1 mg).

M.p.>300° C.

IR (nujol, cm$^{-1}$): 1560

MS (m/z): 658 (MH$^+$)

EXAMPLE 8

N-{6-[2-(5-Bromopyrimidin-2-yloxy)ethoxy]-5-(2-methoxyphenoxy)-2-(2-pyrimidinyl)pyrimidin-4-yl}-2-naphthalenesulfonamide:

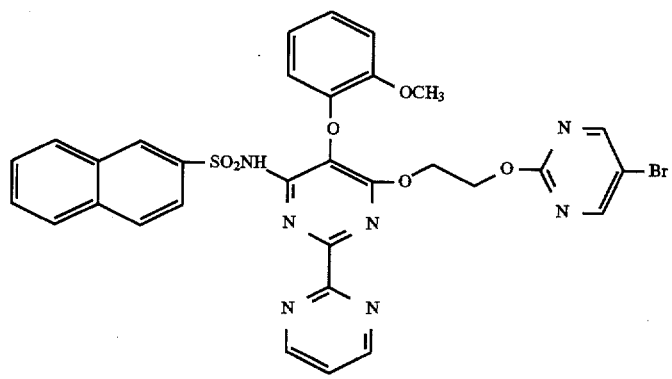

4-Amino-6-[2-(5-bromopyrimidin-2-yloxy)ethoxy]-5-(2-methoxyphenoxy)-2-(2-pyrimidinyl)pyrimidine is treated in the same manner as in Example 7 to give the title compound.

M.p. 163.0°–165.0° C.

IR (nujol, cm$^{-1}$): 1560

MS (m/z): 704 (MH$^+$)

EXAMPLE 9

N-{6-[2-(5-Bromopyrimidin-2-yloxy)ethoxy]-5-(2-methoxyphenoxy)-2-morpholinopyrimidin-4-yl}-2-thiophenesulfonamide:

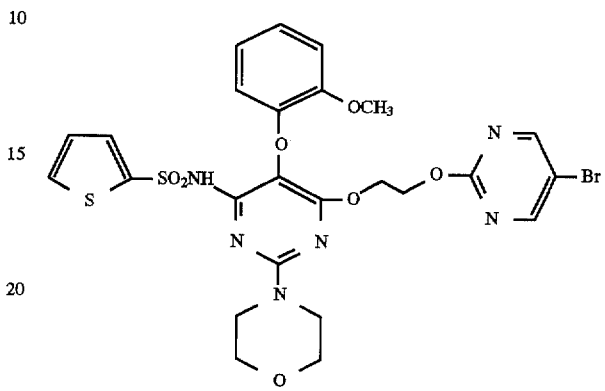

A mixture of 4-amino-6-[2-(5-bromopyrimidin-2-yloxy)ethoxy]-5-(2-methoxyphenoxy)-2-morpholinopyrimidine (200 mg), sodium hydride (60% dispersion, 46.2 mg) and tetrahydrofuran (6 ml) is stirred at room temperature for 20 minutes. To the mixture is added 2-thiophenesulfonyl chloride (211 mg), and the mixture is stirred for 20 hours. The reaction solution is treated with a saturated aqueous ammonium chloride solution, and extracted with ethyl acetate. The ethyl acetate layer is washed, dried, and evaporated under reduced pressure to remove the solvent. The residue is recrystallized from ether-hexane to give the title compound (46 mg).

M.p. 186°–188° C.

EXAMPLE 10

N-{6-[2-(5-Bromopyrimidin-2-yloxy)ethoxy]-5-(2-methoxyphenoxy)-2-morpholinopyrimidin-4-yl}-2-naphthalenesulfonamide:

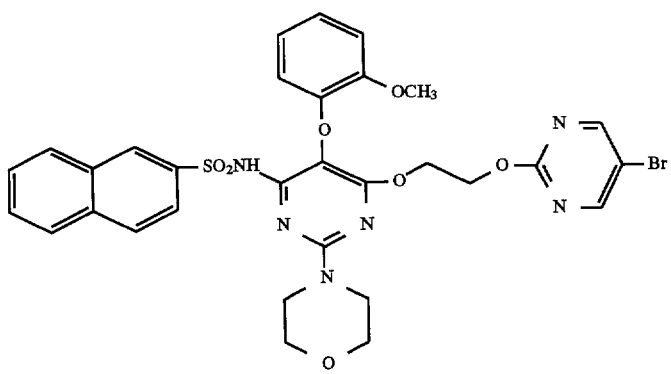

4-Amino-6-[2-(5-bromopyrimidin-2-yloxy)ethoxy]-5-(2-methoxyphenoxy)-2-morpholinopyrimidine is treated in the same manner as in Example 9 to give the title compound.

M.p. 178.0°–181.5° C.

IR (nujol, cm$^{-1}$): 1560, 1460, 1380, 1320

MS (m/z): 709 (MH$^+$)

EXAMPLE 11

4-tert-Butyl-N-{5-(2-benzothienyl)-6-[2-(5-methylthiopyrimidin-2-yloxy)-ethoxy]pyrimidin-4-yl}benzenesulfonamide:

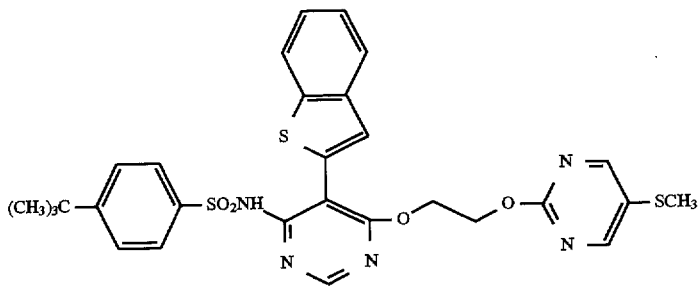

A mixture of N-{5-bromo-6-[2-(5-methylthiopyrimidin-2-yloxy)ethoxy]-pyrimidin-4-yl}-4-tert-butylbenzenesulfonamide (200 mg), 2-benzothienyl tributyltin (460 mg), bis(triphenylphosphine)palladium (II) chloride (51 mg), triphenylphosphine (28 mg), copper (I) bromide (21 mg), a few crystals of 2,6-di-tert-butylcresol and dioxane (6 ml) is refluxed for two hours. After cooling, the reaction solution is diluted with ethyl acetate and an aqueous potassium fluoride solution, and the mixture is stirred at room temperature for 60 minutes. The insoluble materials are removed by filtration, and the filtrate is extracted with ethyl acetate. The ethyl acetate layer is washed, dried, and evaporated under reduced pressure to remove the solvent. The residue is purified by silica gel column chromatography (solvent; methylene chloride:acetone=30:1), and recrystallized from ethyl acetate to give the title compound (182 mg).

M.p. 198.5°–199.5° C.

IR (nujol, cm$^{-1}$): 1610, 1570

MS (m/z): 608 (MH$^+$)

EXAMPLES 12–16

N-{5-Bromo-6-[2-(5-methylthiopyrimidin-2-yloxy)ethoxy]pyrimidin-4-yl}- 4-tert-butylbenzenesulfonamide is treated in the same manner as in Example 11 to give the compounds as listed in Table 2.

TABLE 2

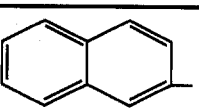

| Ex. No. | Ring B | Physical properties |
|---|---|---|
| 12 | naphthalene | M.p. 187–189° C. |
| 13 | thiophene | M.p. 182–184° C. |
| 14 | pyridine | M.p. 182.5–184.0° C. |
| 15 | methylthiophene | M.p. 160–162° C. |
| 16 | furan | M.p. 175.5–177.0° C. |

EXAMPLE 17

N-{6-(2-(5-Bromopyrimidin-2-yloxy)ethoxy]-5-(2-methoxyphenoxy)-2-methylpyrimidin-4-yl}-2-naphthalenesulfonamide:

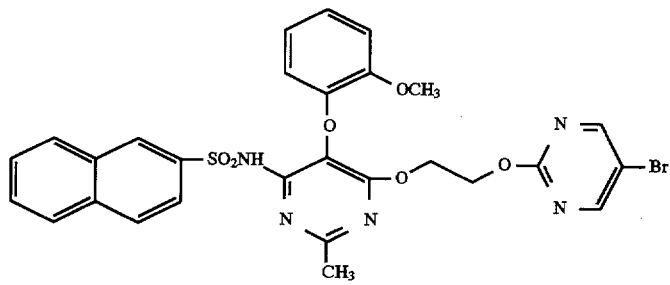

N-{6-(2-Hydroxyethoxy)-5-(2-methoxyphenoxy)-2-methylpyrimidin-4-yl}-2-naphthalenesulfonamide is treated in the same manner as in Example 1 to give the title compound.

M.p. 162.5°–164.5° C.

The compounds of the present invention are exemplified hereinbefore in detail, but the present invention also includes the following compounds as listed in Tables 3 and 4.

TABLE 3
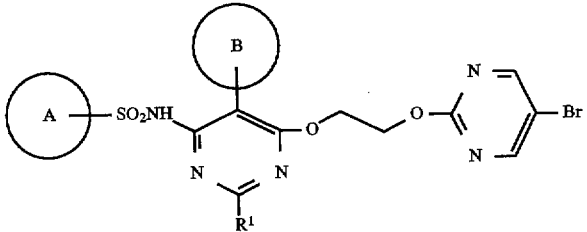
| Ring A | Ring B | R¹ |
|---|---|---|
| 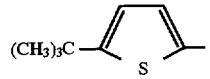 | 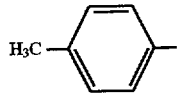 | H |
| 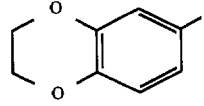 | 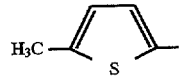 | H |
| 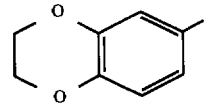 | 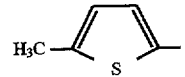 | 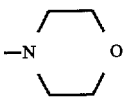 |
| 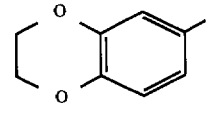 | 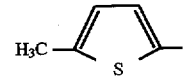 | 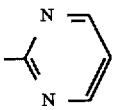 |
| 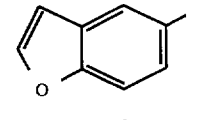 | 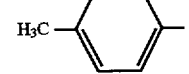 | H |
| 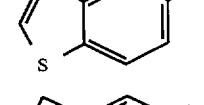 | 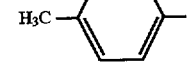 | H |
| 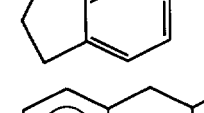 | 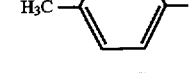 | H |
| 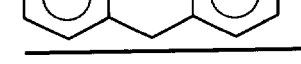 | 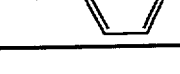 | H |

TABLE 4

[Structure: Ring A—SO₂NH—C(Ring B)=C(—OCH₂CH₂O—R)— with pyrimidine ring bearing R¹ below]

| Ring A | Ring B | R | R¹ |
|---|---|---|---|
| 5-tert-butylthien-2-yl | 2-methoxyphenyl | 5-bromopyrimidin-2-yl | morpholino (—N(CH₂CH₂)₂O) |
| 5-tert-butylthien-2-yl | 2-methoxyphenyl | 5-bromopyrimidin-2-yl | H |
| naphth-2-yl | 2-methoxyphenyl | 5-bromopyrimidin-2-yl | —N(CH₂CH₂)₂NCH₃ (4-methylpiperazin-1-yl) |
| naphth-2-yl | 2-methoxyphenyl | 5-bromopyrimidin-2-yl | —NH(CH₂)₂OH |
| naphth-2-yl | 2-methoxyphenyl | 5-bromopyrimidin-2-yl | 4-hydroxypiperidin-1-yl |
| naphth-2-yl | 2-methoxyphenyl | 5-bromopyrimidin-2-yl | —SCH₂COOH |
| naphth-2-yl | 2-methoxyphenyl | 5-bromopyrimidin-2-yl | —O(CH₂)₂OH |
| naphth-2-yl | 2-methoxyphenyl | 5-(thien-2-yl)pyrimidin-2-yl | morpholino |

EXAMPLE 18

N-{6-[2-(5-Bromopyrimidin-2-yloxy)ethoxy]-2-(2-hydroxyethylamino)-5-(2-methoxyphenoxy)pyrimidin-4-yl}-4-tert-butylbenzenesulfonamide:

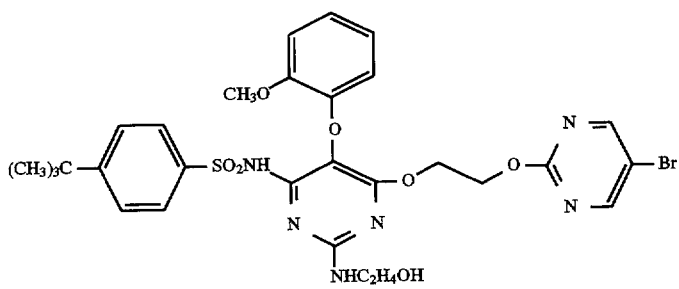

A mixture of N-{6-[2-(5-bromopyrimidin-2-yloxy)ethoxy]-5-(2-methoxy-phenoxy)-2-methylsulfonylpyrimidin-4-yl}-4-tert-butylbenzenesulfonamide (500 mg), ethanolamine (172 mg) and dimethylacetamide (4 ml) is heated with stirring at 110°–120° C. for 20 hours. After cooling, to the mixture is added an aqueous ammonium chloride solution, and the mixture is extracted with ethyl acetate. The extract is washed with water, dried, and evaporated under reduced pressure to remove the solvent. The residue is purified by silica gel column chromatography (solvent; chloroform:ethyl acetate= 3:1) to give the title compound (57 mg) as a powder.

ESI-MS (m/z): 691 (MH$^+$)

IR (nujol, cm$^{-1}$): 3400, 3190

EXAMPLES 19–32

The corresponding starting compounds are treated in the same manner as in Example 18 to give the compounds as listed in Tables 5 and 6.

TABLE 5

| Ex. No. | R$^1$ | Physical properties |
|---|---|---|
| 19 | —S–CH$_2$CH$_2$–OH | ESI—MS(m/z): 708, 706 (MH$^+$) |
| 20 | —S–CH$_2$CH$_2$–CO$_2$CH$_3$ | ESI—MS(m/z): 748, 746 ((M–H)$^+$) |
| 21 | —N(piperidin-4-yl)–OH | M.p. 96.5–100° C. |
| 22 | —NH–CH$_2$CH$_2$CH$_2$–OH | ESI—MS(m/z): 705, 703 (MH$^+$) |
| 23 | —N(CH$_3$)–CH$_2$CH$_2$–OH | M.p. 137–140° C. |
| 24 | —N(piperidin-3-yl)–OH | M.p. 68–70° C. |
| 25 | —S–CH$_2$CH$_2$–COOH | ESI—MS(m/z): 734, 732 ((M–H)$^+$) |
| 26 | —SCH$_3$ | M.p. 108–110° C. |

TABLE 6

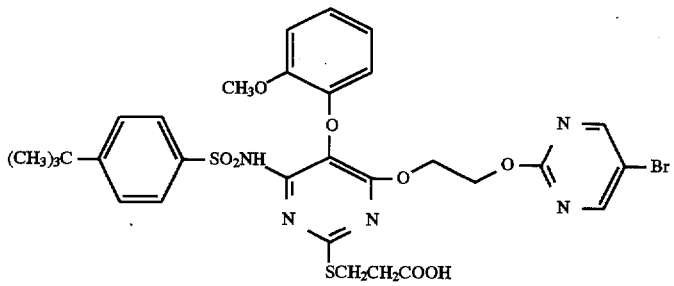

| Ex. No. | R¹ | Physical properties |
|---|---|---|
| 27 | —NH—CH₂—CH(OH)—CH₃ | M.p. 49–53° C. |
| 28 | —O—CH₂—COOH | M.p. 128–133° C. |
| 29 | —NH—CH(CH₂OH)—CH₂OH | — |
| 30 | —S—CH₂CH₂—N(CH₃)₂ | — |
| 31 | —O—CH₂CH₂—N(CH₃)₂ | — |
| 32 | —NH—CH₂CH₂—NH₂ | — |

EXAMPLE 33

3-{6-[2-(5-Bromopyrimidin-2-yloxy)ethoxy]-4-(4-tert-butylbenzene-sulfonamido)-5-(2-methoxyphenoxy)pyrimidin-2-ylthio}propionic acid:

A mixture of the compound obtained in Example 20 (239 mg), bis-tributyltin oxide (570 mg) and toluene (4 ml) is reacted at 90° C. for two days. After cooling, the reaction solution is extracted with ethyl acetate. The extract is washed with water, dried, and evaporated under reduced pressure. The residue is purified by silica gel column chromatography (solvent; n-hexane: ethyl acetate=1:1), and further treated with n-hexane to give the title compound (125 mg) as a powder.

ESI-MS (m/z): 734, 732 (M-H⁺)

IR (nujol, cm⁻¹): 3390, 1730, 1710, 1590, 1560, 1495

EXAMPLE 34

N-{6-[2-(5-Bromopyrimidin-2-yloxy)ethoxy]-2-(2-(N,N-dimethylamino)-ethylamino)-5-(2-methoxyphenoxy)pyrimidin-4-yl}-4-tert-butyl-benzenesulfonamide:

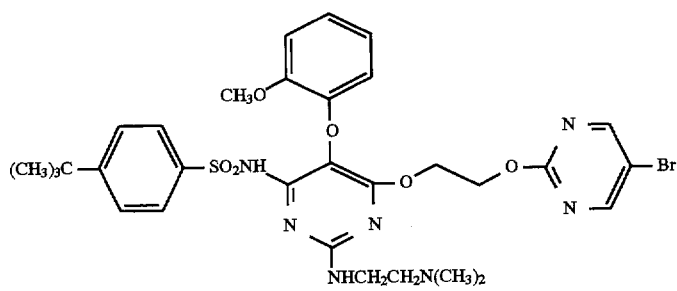

(1) A mixture of 4-tert-butyl-N-{5-(2-methoxyphenoxy)-2-methylsulfonyl-6-[2-(tetrahydropyran-2-yloxy)ethoxy]pyrimidin-4-yl}benzenesulfonamide obtained in Reference Example 10-(2) (200 mg), dimethylaminoethylamine (138.8 mg) and dimethylsulfoxide (1 ml) is reacted at 100° C. for 15 hours, and then reacted at 120° C. for five hours. The reaction mixture is treated with ammonium chloride, and extracted with ethyl acetate. The ethyl acetate layer is washed, dried, and evaporated under reduced pressure. The residue is purified by preparative silica gel thin layer chromatography (solvent; chloroform:methanol=10:1) to give 4-tert-butyl-N-{2-(2-(N,N-dimethylamino)-ethylamino)-5-(2-methoxyphenoxy)-6-[2-(tetrahydropyran-2-yloxy)ethoxy]-pyrimidin-4-yl}benzenesulfonamide (99.7 mg) as a crystal.
M.p. 82°–86° C.

(2) To a solution of the above product (70.6 mg) in methanol (1 ml) is added p-toluenesulfonic acid (12.6 mg), and the mixture is reacted at room temperature for five hours. To the mixture is added sodium hydrogen carbonate (5.5 mg), and the mixture is extracted with chloroform. The extract is washed, dried, and evaporated under reduced pressure to remove the solvent. The residue is purified by preparative silica gel thin layer chromatography (solvent; chloroform:methanol=10:1) to give 4-tert-butyl-N-[2-(2-(N,N-dimethylamino)ethylamino)-6-(2-hydroxyethoxy)-5-(2-methoxy-phenoxy)pyrimidin-4-yl]benzenesulfonamide (46.3 mg) as a crystal.
M.p. 102.5°–106° C.

(3) To a solution of the above product (37.3 mg) in tetrahydrofuran (2 ml) is added sodium hydride (60% dispersion, 4 mg), and thereto is added 5-bromo-2-chloropyrimidine (52 mg), and the mixture is stirred at room temperature for one hour. The reaction solution is neutralized with ammonium chloride, and extracted with ethyl acetate. The ethyl acetate layer is washed, dried, and evaporated under reduced pressure. The residue is purified by preparative silica gel thin layer chromatography (solvent; chloroform:ethyl acetate=1:2) to give the title compound (24.6 mg) as a crystal.
M.p. 129°–132.5° C.

EXAMPLES 35–42

The corresponding starting compounds are treated in the same manner as in Example 34 to give the compounds as listed in Table 7.

TABLE 7

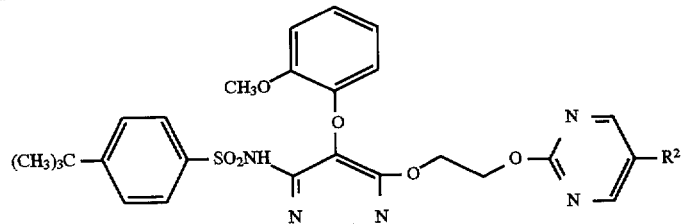

| Ex. No. | R¹ | R² | Physical properties |
|---|---|---|---|
| 35 | —OCH₃ | Br | M.p. 78–80° C. |
| 36 | —SCH₂COOH | Br | M.p. >300° C. |
| 37 | —NH–CH₂CH₂–OCH₃ | Br | M.p. 69.0–73.5° C. |
| 38 | —NH–CH₂CH₂–OCH₃ | OCH₃ | M.p. 126.5–128.5° C. |
| 39 | —NH–CH₂CH₂–COOH | Br | — |
| 40 | —NH–CH₂–COOH | Br | — |

TABLE 7-continued

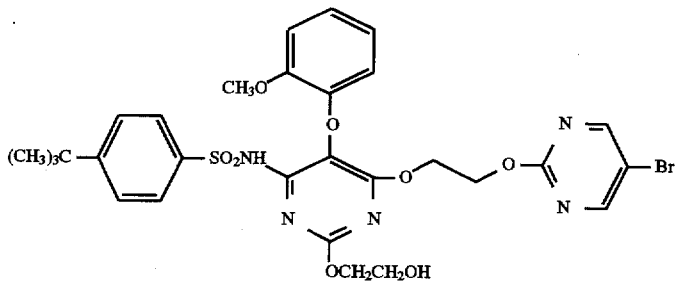

| Ex. No. | R¹ | R² | Physical properties |
|---|---|---|---|
| 41 | —CH₂CH₂COOH | Br | — |
| 42 | —CH₂CH₂OH | Br | — |

EXAMPLE 43

N-{6-[2-(5-Bromopyrimidin-2-yloxy)ethoxy]-2-(2-hydroxyethoxy)-5-(2-methoxyphenoxy)pyrimidin-4-yl}-4-tert-butylbenzenesulfonamide:

(1) To ethylene glycol (2 ml) is added sodium hydride (60% dispersion, 125.8 mg). To this mixture is added 4-tert-butyl-N-{5-(2-methoxyphenoxy)-2-methylsulfonyl-6-[2-(tetrahydropyran-2-yloxy)ethoxy]pyrimidin-4-yl}benzene-sulfonamide obtained in Reference Example 10-(2) (500 mg), and the mixture is stirred at room temperature for 18 hours. To the reaction solution is added an aqueous ammonium chloride solution, and the mixture is extracted with ethyl acetate. The ethyl acetate layer is washed with water, dried, and evaporated under reduced pressure to remove the solvent. The residue is purified by silica gel column chromatography (solvent; chloroform:ethyl acetate= 1:1) to give 4-tert-butyl-N-{2-(2-hydroxyethoxy)-5-(2-methoxy-phenoxy)-6-[2-(tetrahydropyran-2-yloxy)ethoxy]pyrimidin-4-yl}benzene-sulfonamide (440.5 mg) as a colorless caramel.

ESI-MS (m/z): 61 8 (MH⁺)
IR (nujol, cm⁻¹): 3600–3050, 1570, 1460, 1340

(2) A solution of the above product (425 mg), tert-butyldiphenylsilyl chloride (208 mg), 4-dimethylaminopyridine (3.42 mg) and triethylamine (83.6 mg) in methylene chloride (3 ml) is stirred at room temperature for 18 hours. The mixture is diluted with chloroform, and the mixture is washed with water, dried, and evaporated under reduced pressure to remove the solvent. The residue is dissolved in a mixture of methanol (5 ml) and tetrahydrofuran (5 ml), and thereto is added p-toluenesulfonic acid (100 mg), and the mixture is stirred at room temperature for one hour. The mixture is neutralized with sodium hydrogen carbonate, and extracted with ethyl acetate. The extract is washed with water, dried, and evaporated under reduced pressure to remove the solvent. The residue is purified by silica gel column chromatography (solvent; n-hexane:ethyl acetate=2:1~1:1) to give 4-tert-butyl-N-[2-(2-tertbutyldiphenylsilyloxyethoxy)-6-(2-hydroxyethoxy)-5-(2-methoxyphenoxy)-pyrimidin-4-yl]benzenesulfonamide (548 mg) as a colorless oil.

ESI-MS (m/z): 772 (MH⁺)
IR (neat, cm⁻¹): 3600–3100, 1580, 1460, 1430, 1350

(3) To a solution of the above product (240.7 mg) in tetrahydrofuran (5 ml) is added sodium hydride (60% dispersion, 37.4 mg), and the mixture is stirred at room temperature for 15 minutes. To the mixture is added 5-bromo-2-chloropyrimidine (90.4 mg), and the mixture is stirred at room temperature for two hours. To the reaction solution is added an aqueous ammonium chloride solution, and the mixture is extracted with ethyl acetate. The ethyl acetate layer is washed, dried, and evaporated under reduced pressure to remove the solvent. The residue is purified by preparative silica gel thin layer chromatography (solvent; n-hexane:ethyl acetate=3:2) to give N-{6-[2-(5-bromo-pyrimidino2-yloxy)ethoxy]-2-(2-tert-butyldiphenylsilyloxyethoxy)-5-(2-methoxy-phenoxy)pyrimidin-4-yl}-4-tert-butylbenzenesulfonamide (132.4 mg) as a colorless oil.

ESI-MS (m/z): 929 (MH⁺)

(4) To a solution of the above product (82.9 mg) in tetrahydrofuran (3 ml) is added a 1.0M solution of tetrabutylammonium fluoride in tetrahydrofuran (0.09 ml), and the mixture is stirred at room temperature for one hour. The mixture is evaporated under reduced pressure to remove the solvent, and extracted with ethyl acetate. The ethyl acetate layer is washed, dried, and evaporated under reduced pressure to remove the solvent. The residue is treated with n-hexane to give the title compound (49 mg) as a crystal.

M.p. 73.5°–77° C.

EXAMPLE 44

N-{6-[2-(5-Bromopyrimidin-2-yloxy)ethoxy]-2-hydroxymethyl-5-(2-methoxyphenoxy)pyrimidin-4-yl}-4-tert-butylbenzenesulfonamide:

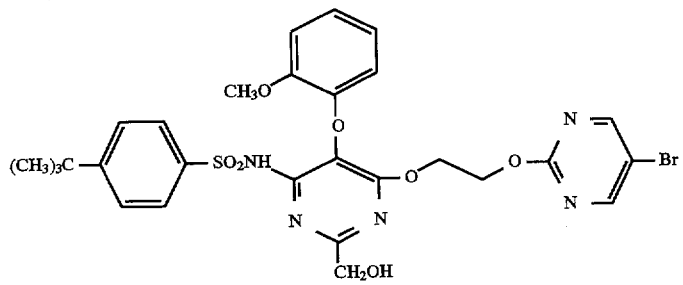

(1) To a solution of methoxymethyloxymethyltributyltin (655 mg) in tetrahydrofuran (6 ml) is added dropwise a 1.63M solution of n-butyl lithium in n-hexane (1.09 ml) at −78° C. The mixture is stirred at the same temperature for four minutes, and thereto is added a solution of 4-tert-butyl-N-[6-(2-hydroxy-ethoxy)-5-(2-methoxyphenoxy)-2-methylsulfonylpyrimidin-4-yl] benzenesulfonamide obtained in Reference Example 10-(1) (200 mg) in tetrahydrofuran (2 ml), and the mixture is stirred for 40 minutes. To the mixture is added an aqueous ammonium chloride solution, and the mixture is extracted with ethyl acetate. The ethyl acetate layer is washed, dried, and evaporated under reduced pressure to remove the solvent. The residue is purified by silica gel column chromatography (solvent; chloroform:methanol=100:1~50:1) to give 4-tert-butyl-N-[6-(2-hydroxyethoxy)-2-methoxymethyloxymethyl-5-(2-methoxy-phenoxy)pyrimidin-4-yl] benzenesulfonamide (111 mg) as a colorless caramel.

ESI-MS (m/z): 546 (MH+)

IR (neat, cm$^{-1}$): 3550–3400, 3200, 1580, 1500, 1480, 1430

(2) To a solution of the above product (80 mg) in a mixture of tetrahydrofuran (2 ml) and dimethylformamide (0.4 ml) is added sodium hydride (60% dispersion, 18 mg), and thereto is added 5-bromo-2-chloropyrimidine (42 mg), and the mixture is stirred at room temperature for one hour. To the reaction solution is added an aqueous ammonium chloride solution, and the mixture is extracted with ethyl acetate. The ethyl acetate layer is washed, dried, and evaporated under reduced pressure to remove the solvent. The residue is purified by preparative silica gel thin layer chromatography (solvent; chloroform:ethyl acetate=3:1) to give N-{6-[2-(5-bromopyrimidin-2-yloxy)-ethoxy]-2-methoxymethyloxymethyl-5-(2-methoxyphenoxy) pyrimidin-4-yl}-4-tert-butylbenzenesulfonamide (91 mg) as a foam.

ESI-MS (m/z): 706, 704 (MH+)

(3) To a solution of the above product (85 mg) in methylene chloride (2 ml) is added trifluoroacetic acid (11 ml), and the mixture is stirred at room temperature overnight. The mixture is evaporated under reduced pressure to remove the solvent, and the residue is purified by preparative silica gel thin layer chromatography (solvent; chloroform:methanol=30:1 ), and recrystallized from ethyl acetate-n-hexane to give the title compound (26 mg) as a crystal.

M.p. 161°–162° C.

EXAMPLE 45

N-[2-Amino-6-{2-(5-bromopyrimidin-2-yloxy)ethoxy}-5-(2-methoxy-phenoxy)pyrimidin-4-yl]-4-tert-butylbenzenesulfonamide:

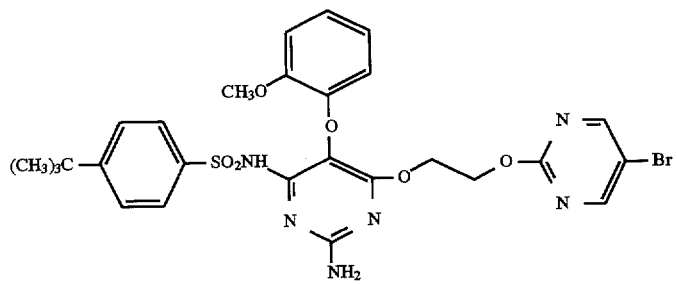

(1) A mixture of N-[6-{2-(5-bromopyrimidin-2-yloxy) ethoxy}-5-(2-methoxy-phenoxy)-2-methylsulfonylpyrimidin-4-yl]-4-tert-butylbenzenesulfonamide obtained in Reference Example 9-(6) (300 mg), sodium azide (92 mg) and dimethylformamide (2 ml) is heated with stirring at 80° C. for one hour. After cooling, to the mixture is added water, and the mixture is extracted with ethyl acetate. The ethyl acetate layer is washed with water, dried, and evaporated under reduced pressure to remove the solvent. The residue is purified by preparative silica gel thin layer chromatography (solvent; chloroform:ethyl acetate=2:1) to give N-[2-azideo6-{2-(5obromopyrimidin-2-yloxy)ethoxy}-5-(2-methoxyphenoxy)pyrimidin-4-yl]-4-tert-butylbenzenesulfonamide (323.3 mg) as a foamy.

ESI-MS (m/z): 673 (MH$^+$)

IR (nujol, cm$^{-1}$): 3400–2800, 2140, 1680, 1600–1560, 1500, 1460

(2) A mixture of the above product (293.3 mg), triphenylphosphine (127.1 mg) and tetrahydrofuran (2 ml) is stirred at room temperature for 15 minutes. The mixture is extracted with chloroform, and the extract is washed with water, dried, and evaporated under reduced pressure to remove the solvent. The residue is purified by silica gel column chromatography (solvent; chloroform: ethyl acetate=2:1) to give a triphenylphosphine-addition compound (317.5 mg). To a solution of the product (275 mg) in tetrahydrofuran (2 ml) is added p-toluenesulfonic acid (17 mg), and the mixture is stirred at room temperature for 12 hours. The mixture is neutralized with an aqueous sodium hydrogen carbonate solution, and extracted with ethyl acetate. The ethyl acetate layer is washed, dried, and evaporated under reduced pressure to remove the solvent. The residue is purified by preparative silica gel thin layer chromatography (solvent; ethyl acetate:n-hexane=3:1) to give the title compound (121.6 mg) as a crystal.

M.p. 197°–198.5° C.

EXAMPLE 46

N-[6-{2-(5-Bromopyrimidin-2-yloxy)ethoxy}-2-(2-hydroxyethylamino)-5-(4-methylphenyl)pyrimidin-4-yl]-4-tert-butylbenzenesulfonamide:

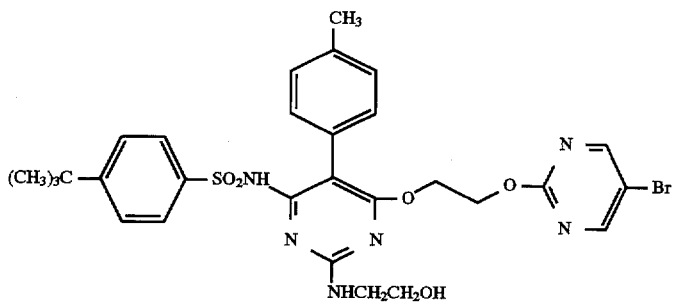

(1) A solution of N-[6-(2-benzyloxyethoxy)-5-(4-methylphenyl)-2-methylsulfonylpyrimidin-4-yl]-4-tert-butylbenzenesulfonamide obtained in Reference Example 11-(6) (300 mg) in 2-aminoethanol (4 ml) is heated with stirring at 120° C. for three hours. After cooling, to the reaction solution is added an aqueous ammonium chloride solution, and the mixture is extracted with ethyl acetate. The ethyl acetate layer is washed with water, dried, and evaporated under reduced pressure to remove the solvent. The residue is purified by silica gel column chromatography (solvent; chloroform:methanol=10:1), and recrystallized from isopropyl ether-n-hexane to give N-[6-{2-benzyloxyethoxy)-2-(2-hydroxyethylamino)-5-(4-methylphenyl)pyrimidin-4-yl]-4-tert-butylbenzenesulfonamide (260 mg) as a crystal.

M.p. 124°–126° C.

(2) To a solution of the above product (245 mg) and 3,4-dihydro-2H-pyran (0.1 ml) in methylene chloride (4 ml) is added 10-camphorsulfonic acid (4 mg), and the mixture is stirred at room temperature for 6 hours. The reaction solution is treated with a diluted aqueous sodium hydrogen carbonate solution, and extracted with ethyl acetate. The ethyl acetate layer is washed with water, dried, and evaporated under reduced pressure to remove the solvent. The residue is purified by silica gel column chromatography (solvent; ethyl acetate:n-hexane=1:10~1:3) to give N-{6-(2-benzyloxyethoxy)-5-(4-methylphenyl)-2-[2-(tetrahydropyran-2-yloxy)ethylamino]-pyrimidin-4-yl}-4-tert-butylbenzenesulfonamide (234 mg) as a caramel.

ESI-MS (m/z): 675 (MH$^+$)

IR (nujol, cm$^{-1}$): 1460, 1380, 1080

(3) A mixture of the above product (220 mg), palladium-carbon (150 mg), methanol (4 ml) and tetrahydrofuran (2 ml) is subjected to catalytic hydrogenation for 1.5 hour under hydrogen atmosphere. The catalyst is removed by filtration, and the filtrate is concentrated under reduced pressure. The residue is recrystallized from n-hexane to give 4-tert-butyl-N-{6-(2-hydroxyethoxy)-5-(4-methylphenyl)-2-[2-(tetrahydropyran-2-yloxy)ethylamino]-pyrimidin-4-yl}benzenesulfonamide (167 mg).

M.p. 113°–116° C.

(4) To a mixture of the above product (154 mg), tetrahydrofuran (5 ml) and dimethylacetamide (3 ml) is added sodium hydride (60% dispersion, 63 mg), and the mixture is stirred for five minutes. To the mixture is added 5-bromo-2-chloropyrimidine (142 mg), and the mixture is stirred at room temperature for 19 hours. The mixture is treated with an aqueous ammonium chloride solution, and extracted with ethyl acetate. The ethyl acetate layer is washed with water, dried, and evaporated under reduced pressure to remove the solvent. The residue is purified by silica gel column chromatography (solvent; chloroform:ethyl acetate=40:1), and recrystallized from n-hexane to give N-{6-[2-(5-bromopyrimidin-2-yloxy)ethoxy]-5-(4-methylphenyl)-2-[2-(tetrahydro-pyran-2-yloxy)ethylamino]pyrimidin-4-yl}-4-tert-butylbenzenesulfonamide (141 mg).

M.p. 65°–69° C.

(5) To a solution of the above product (124 mg) in methanol (5 ml) is added 10% aqueous hydrochloric acid solution, and the mixture is reacted at room temperature for two hours. The mixture is neutralized with sodium hydrogen carbonate, and extracted with ethyl acetate. The extract is washed with water, dried, and evaporated under reduced pressure to remove the solvent. The residue is purified by silica gel column

EXAMPLE 47

N-{6-[2-(5-Bromopyrimidin-2-yloxy)ethoxy]-5-(2-methoxyphenoxy)-2-(5-tetrazolyl)pyrimidin-4-yl}-4-tert-butylbenzenesulfonamide:

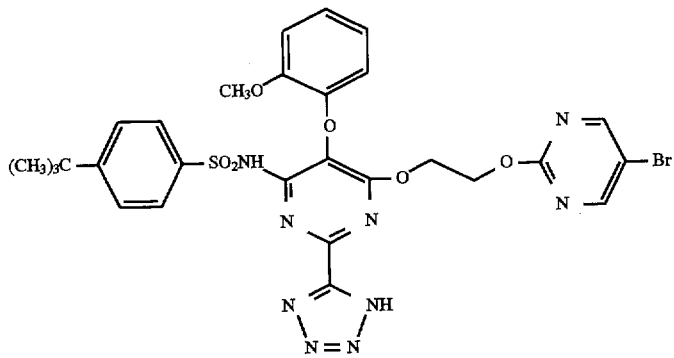

(1) A mixture of 4-tert-butyl-N-{5-(2-methoxyphenoxy)-2-methylsulfonyl-6-[2-(tetrahydropyran-2-yloxy)ethoxy]pyrimidin-4-yl}benzenesulfonamide obtained in Reference Example 10-(2) (500 mg), potassium cyanide (153 mg) and dimethylformamide (5 ml) is heated with stirring at 120° C. for three hours. After cooling, to the reaction solution is added an aqueous ammonium chloride solution, and the mixture is extracted with ethyl acetate. The extract is washed with water, dried, and evaporated under reduced pressure to remove the solvent to give 4-tert-butyl-N-{2-cyano-5-(2-methoxyphenoxy)-6-[2-(tetrahydropyran-2-yloxy)ethoxy]pyrimidin-2-yl}benzenesulfonamide (425 mg) as a crystal.

(2) To a solution of the above product (392 mg) in methanol (5 ml) is added p-toluenesulfonic acid (13 mg), and the mixture is reacted at room temperature for two hours. The reaction solution is treated with water, and extracted with ethyl acetate. The ethyl acetate layer is washed with water, dried, and evaporated under reduced pressure to remove the solvent to give 4-tert-butyt-N-{2-cyano-6-(2-hydroxyethoxy)-5-(2-methoxyphenoxy)pyrimidin-4-yl}benzenesulfonamide (294 mg) as a foamy product.

(3) To a mixture of the above product (266 mg), tetrahydrofuran (3 ml) and dimethylacetamide (0.5 ml) is added sodium hydride (60% dispersion, 54 mg), and the mixture is stirred for 10 minutes. To the mixture is added 5-bromo-2-chloropyrimidine (131 mg), and the mixture is stirred at room temperature for one hour. The mixture is treated with an aqueous ammonium chloride solution, and extracted with ethyl acetate. The ethyl acetate layer is washed with water, dried, and evaporated under reduced pressure to remove the solvent. The residue is purified by silica gel column chromatography (solvent; chloroform:ethyl acetate=10:1), and recrystallized from ethyl acetate-n-hexane to give N-{6-[2-(5-bromopyrimidin-2-yloxy)ethoxy]-2-cyano-5-(2-methoxyphenoxy)pyrimidin-4-yl}-4-tert-butylbenzenesulfonamide (206 mg) as a powder.

(4) A mixture of the above product (188 mg), tributyltin azide (182 mg) and toluene (3 ml) is refluxed for 23 hours. The mixture is evaporated under reduced pressure to remove the solvent, and the residue is purified by silica gel column chromatography (solvent; chloroform:methanol=40:1~10:1) to give the title compound (68 mg) as a powder.

ESI-MS (m/z): 698, 696 (NH$^+$)

IR (nujol, cm$^{-1}$): 3350, 3190, 1570, 1460

REFERENCE EXAMPLE 1

(1) To a mixture of tetrahydrofuran (400 ml) and ethylene glycol (60 ml) is added with stirring sodium hydride (60% dispersion, 3.38 g) under ice-cooling, and thereto is added 4,6-dichloro-5-(4-methylphenyl)pyrimidine (20.0 g). The mixture is stirred under ice-cooling for 30 minutes, and then stirred at room temperature for two hours. The mixture is weakly acidified with acetic acid, and concentrated under reduced pressure. The residue is dissolved in ethyl acetate, and washed, dried, and concentrated to dryness under reduced pressure. The residue is crystallized from hexane to give 2-{6-chloro-5-(4-methylphenyl)pyrimidin-4-yloxy}ethanol (21.85 g).

M.p. 62°–64° C.

(2) A mixture of the above product (21.85 g), sodium azide (10.7 g) and dimethylformamide (260 ml) is heated with stirring at 75°–80° C. overnight. After cooling, the mixture is treated with water, and extracted with ethyl acetate. The ethyl acetate layer is washed with water, dried, and evaporated under reduced pressure to remove the solvent. The residue is crystallized from hexane to give 2-{6-azido-5-(4-methylphenyl)pyrimidin-4-yloxy}ethanol (19.6 g).

M.p. 83.5°–85° C.

MS (m/z): 271 (M$^+$)

(3) A mixture of the above product (19.6 g), 10% palladium-carbon (50% wet, 4.0 g) and ethanol (240 ml) is subjected to catalytic reduction at room temperature for one hour under hydrogen atmosphere (1 atm). The catalyst is removed by filtration, and the filtrate is concentrated under reduced pressure. The residue is recrystallized from ethyl acetate-hexane to give 2-{6-amino-5-(4-methylphenyl)pyrimidin-4-yloxy}ethanol (15.9 g).

M.p. 104°–105° C.

REFERENCE EXAMPLE 2

(1) To a solution of 4,6-dichloro-5-(4-methylphenyl) pyrimidine (4.14 g) in ether (20 ml) is added 27% ammonia in methanol solution (30 ml), and the mixture is reacted at room temperature for three days in a sealed tube. The mixture is evaporated under reduced pressure to remove the solvent, and the residue is purified by silica gel column chromatography (solvent; hexane::ethyl acetate=10:1~ethyl acetate only) to give 4-amino-6-chloro-5-(4-methyl-phenyl)pyrimidine (1.89 g).

M.p. 168°–171° C.

(2) A mixture of 4-amino-6-chloro-5-(4-methylphenyl) pyrimidine (500 mg), ethylene glycol (10 ml) and sodium hydride (60% dispersion, 0.46 g) is reacted at 70° C. for two hours, and then reacted at 90° C. for five hours. The reaction mixture is treated with a saturated ammonium chloride solution, and extracted with ethyl acetate. The ethyl acetate layer is washed, dried, and evaporated under reduced pressure to remove the solvent. The residue is crystallized from hexane-ethyl acetate to give 2-{6-amino-5-(4-methylphenyl)-pyrimidin-4-yloxy}ethanol (422 mg).

M.p. 91.5°–93.5° C.

REFERENCE EXAMPLE 3

To a solution of 2-{6-amino-5-(4-methylphenyl)pyrimidin-4-yloxy}-ethanol (7.54 g)in tetrahydrofuran (150 ml) is added sodium hydride (60% dispersion, 1.47 g), and thereto is added 5-bromo-2-chloropyrimidine (7.73 g), and the mixture is stirred at room temperature overnight. To the reaction solution is added a saturated aqueous ammonium chloride solution, and the mixture is evaporated under reduced pressure to remove the solvent. The precipitated crystals are collected by filtration, washed, and dried. The crude crystals are purified by silica gel column chromatography (solvent; chloroform: methanol=100:1~80:1), and recrystallized from tetrahydrofuran-diethyl ether to give 4-amino-6-[2-(5-bromopyrimidin-2-yloxy)ethoxy]-5-(4-methyl-phenyl)pyrimidine (11.27 g).

M.p. 178.5°–179.5° C.

IR (nujol, cm$^{-1}$): 3400, 3300, 3130, 1640, 1580

MS (m/z): 401, 403 (M$^+$)

REFERENCE EXAMPLE 4

(1) To a solution of 4,6-dichloropyrimidine (1.33 g) and 4-tert-butylbenzene-sulfonamide (1.96 g) in dimethyl-sulfoxide (20 ml) is added sodium hydride (60% dispersion, 714 mg), and the mixture is stirred at room temperature for two hours. The reaction solution is diluted with 10% hydrochloric acid and water, and extracted with ethyl acetate. The ethyl acetate layer is washed, dried, and evaporated under reduced pressure to remove the solvent. The residue is recrystallized from ethyl acetate to give 4-tert-butyl-N-(6-chloropyrimidin-4-yl)-benzenesulfonamide (2.02 g).

M.p. 225°–226.5° C.

IR (nujol, cm$^{-1}$): 3035, 1630, 1595, 1575

MS (m/z): 325 (M$^+$)

(2) To ethylene glycol (20 ml)is added sodium hydride (60% dispersion, 1.03 g), and thereto is added the above product (1.66 g), and the mixture is stirred at 60° C. for 20 hours. After cooling, the mixture is acidified with 10% hydrochloric acid, and extracted with ethyl acetate. The ethyl acetate layer is washed, dried, and evaporated under reduced pressure to remove the solvent. The residue is crystallized from ethyl acetate to give 4-tert-butyl-N-[6-( 2-hydroxyethoxy)pyrimidin-4-yl)benzenesulfonamide (1.58 g).

M.p. 169°–170.5° C.

IR (nujol, cm$^{-1}$): 3440, 1600, 1570

MS (m/z): 352 (MH$^+$)

(3) To a solution of the above product (210 mg) in dimethylformamide (4 ml) is added N-bromosuccinimide (116 mg), and the mixture is stirred at room temperature for one hour. The mixture is treated with an aqueous sodium hydrogen sulfite, and extracted with ethyl acetate. The ethyl acetate layer is washed, dried, and evaporated under reduced pressure to remove the solvent. The residue is purified by silica gel column chromatography (solvent; chloroform:methanol=40:1), and recrystallized from hexane-ethyl acetate to give N-[5-bromo-6-(2-hydroxyethoxy)pyrimidin-4-yl]-4-tert-butylbenzene-sulfonamide (169 mg).

M.p. 146°–147.5° C.

IR (nujol, cm$^{-1}$): 3360, 3200, 1620, 1575

MS (m/z): 432, 430 (MH$^+$)

(4) To a solution of the above product (3.10 g) in dimethylacetamide (30 ml) is added sodium hydride (60% dispersion, 720 mg), and the mixture is stirred at room temperature for 30 minutes. To the mixture is added 2-chloro-5-methylthiopyrimidine (1.51 g), and the mixture is stirred at room temperature overnight. The reaction solution is treated with 10% hydrochloric acid and a saturated aqueous ammonium chloride solution, and extracted with ethyl acetate. The ethyl acetate layer is washed, dried, and evaporated under reduced pressure to remove the solvent. The residue is purified by silica gel column chromatography (solvent; chloroform:ethyl acetate=10:1 ); and recrystallized from hexane-ethyl acetate to give N-{5-bromo-6-[2-(5-methylthio-pyrimidin-2-yloxy)ethoxy]pyrimidin-4-yl}-4-tert-butylbenzenesulfonamide (3.34 g).

M.p. 120°–121° C.

IR (nujol, cm$^{-1}$): 1585, 1575, 1550

MS (m/z): 556, 554 (MH$^+$)

REFERENCE EXAMPLE 5

(1) To a mixture of 4,6-dichloropyrimidine (5.0 g), ethylene glycol (100 ml) and tetrahydrofuran (100 ml) is added sodium hydride (60% dispersion, 1.34 g) under ice-cooling, and the mixture is stirred at the same temperature for two hours, and evaporated under reduced pressure to remove the solvent. The residue is extracted with ethyl acetate, and the extract is dried, and concentrated under reduced pressure. The residue is purified by silica gel column chromatography (solvent; chloroform:ethyl acetate=5:1~2:1) to give 2-(6-chloropyrimidin-4-yloxy)ethanol (5.67 g) as an oily product.

IR (nujol, cm$^{-1}$): 3300, 1575, 1545

MS (m/z): 175 (MH$^+$)

(2) To a solution of the above product (5.61 g) in dimethylformamide (60 ml) is added sodium azide (4.18 g), and the mixture is heated with stirring at 70° C. for 20 hours. After cooling, the reaction solution is treated with water, and extracted with ethyl acetate. The ethyl acetate layer is dried, and evaporated under reduced pressure to remove the solvent. The residue is purified by silica gel column chromatography (solvent; hexane:ethyl acetate=1:1) to give 2-(6-azidopyrimidin-4-yloxy)ethanol (1.68 g).

M.p. 49°–50° C.

IR (nujol, cm$^{-1}$): 3280, 2070, 1600, 1550

MS (m/z): 181 (MH⁺)

(3) A mixture of the above product (1.64 g), 10% palladium-carbon (0.25 g) and ethanol (20 ml) is subjected to catalytic reduction at room temperature for one hour under hydrogen atmosphere (1 atm). The catalyst is removed by filtration, and the filtrate is concentrated. The residue is recrystallized from ethanol-diethyl ether to give 2-(6-aminopyrimidin-4-yloxy)ethanol (1.11 g).

M.p. 133°–137° C.
IR (nujol, cm⁻¹): 3360, 3200, 1660, 1610, 1550
MS (m/z): 156 (MH⁺)

(4) To a suspension of the above product (400 mg) in methanol (4 ml) is added dropwise a solution of bromine (437 mg) in methanol (2 ml). The mixture is evaporated under reduced pressure to remove the solvent, and the residue is dissolved in ethyl acetate. The mixture is treated with a saturated aqueous sodium hydrogen carbonate solution, and extracted with ethyl acetate-tetrahydrofuran. The organic layer is washed, dried, and evaporated under reduced pressure to remove the solvent to give 2-(6-amino-5-bromo-pyrimidin-4-yloxy)ethanol (632 mg).

IR (nujol, cm⁻¹): 3480, 3420, 3390, 3290, 1640, 1580
MS (m/z): 235, 233 (M⁺)

(5) To a solution of the above product (611 mg) in dimethylformamide (20 ml) is added sodium hydride (60% dispersion, 125 mg), and the mixture is stirred for 20 minutes. To the mixture is added 2-chloro-5-methylthio-pyrimidine (461 mg), and the mixture is stirred at room temperature for three hours. To the mixture is added ice-water, and the mixture is extracted with ethyl acetate. The ethyl acetate layer is washed, dried, and evaporated under reduced pressure to remove the solvent. The residue is purified by silica gel column chromatography (solvent; chloroform:methanol=20:1), and recrystallized from ethyl acetate-diisopropyl ether to give 4-amino-5-bromo-6-2-(5-methylthiopyrimidin-2-yloxy)ethoxy]pyrimidine (501 mg).

M.p. 126°–129° C.
IR (nujol, cm⁻¹): 3450, 3270, 1635, 1585, 1570, 1540
MS (m/z): 359, 357 (MH⁺)

(6) To a solution of the above product (102 mg) in tetrahydrofuran (2 ml) is added sodium hydride (60% dispersion, 34 mg), and thereto is added 4-tert-butylbenzenesulfonyl chloride (198 mg), and the mixture is stirred at room temperature for 20 minutes. To the mixture are added a drop of pyridine, and water, and the mixture is stirred at room temperature for 30 minutes. The mixture is neutralized with a saturated aqueous ammonium chloride solution, and extracted with ethyl acetate. The ethyl acetate layer is washed, dried, and evaporated under reduced pressure to remove the solvent. The residue is purified by preparative silica gel thin layer chromatography (solvent; chloroform:methanol=15:1 ), and recrystallized from hexane-ethyl acetate to give N-{5-bromo-6-[2-(5-methylthiopyrimidin-2-yloxy)ethoxy]Pyrimidin-4-Yl}-4-tert-butylbenzenesulfonamide (135 mg). The physical properties of the compound are the same as those of the compound obtained in Reference Example 4-(4).

REFERENCE EXAMPLE 6

(1) To a solution of (2-thienyl)malonic acid diethyl ester (18.0 g) and 2-pyrimidinylamidine hydrochloride (10.02 g) in methanol is added a 28% solution of sodium methoxide (36.58 g) in methanol (30 ml) under ice-cooling, and the mixture is stirred at room temperature for 16 hours. After the reaction is completed, the reaction solution is concentrated, and acidified with 10% hydrochloric acid. The mixture is stirred for 30 minutes, and the precipitated crystals are collected by filtration, washed, and dried to give 5-(2-thienyl)-4,6-dihydroxy-2-(2-pyrimidinyl)pyrimidine (5.15 g) as a crystalline powder.

M.p. 244°–246° C.
IR (nujol, cm⁻¹): 1635, 1600
MS (m/z): 272 (M⁺)

(2) A mixture of the above product (5.00 g), N-diethylaniline (15 ml) and phosphorus oxychloride (50 ml) is heated with stirring at 80° C. for two hours, and then heated with stirring at 90° C. for 3.5 hours. After the reaction is completed, the mixture is evaporated under reduced pressure to remove the phosphorus oxychloride, and the residue is slowly poured into water (300 ml). The mixture is stirred at room temperature, and extracted with ethyl acetate. The extract is washed, dried, and evaporated under reduced pressure to remove the solvent. The residue is purified by silica gel column chromatography (solvent; chloroform:ethyl acetate=5:1) to give 5-(2-thienyl)-4,6-dichloro-2-(2-pyrimidinyl)pyrimidine (2.77 g) as a crystal.

M.p. 159°–160° C.
IR (nujol, cm⁻¹): 1560
MS (m/z): 308 (M+)

(3) To a suspension of the above product (2.77 g) in dimethylsulfoxide (30 ml) are added 4-tert-butylbenzenesulfonamide (2.30 g) and potassium carbonate (6.19 g), and the mixture is heated with stirring at 80° C. for 8 hours. After cooling, the reaction mixture is acidified with iced 10% hydrochloric acid, and extracted with ethyl acetate. The extract is washed, dried, and evaporated under reduced pressure to remove the solvent. The residue is purified by flash silica gel column chromatography (solvent; hexane:ethyl acetate=1:1 ), and crystallized from n-hexane-ethyl acetate to give 4-tert-butyl-N-[6-chloro-5-(2-thienyl)-2-(2-pyrimidinyl)pyrimidin-4-yl]benzenesulfonamide (1.67 g) as a powder.

M.p. 129.5°–131.5° C.
IR (nujol, cm⁻¹): 1640, 1560
MS (m/z): 486 (M⁺)

(4) To ethylene glycol (20 ml) is added sodium hydride (60% dispersion, 688 mg), and thereto is added the above product (1672 mg). The reaction solution is stirred at room temperature for 20 minutes, and reacted at 140° C. for 3.5 hours. After cooling, the reaction solution is acidified with 10% hydrochloric acid, and extracted with ethyl acetate. The ethyl acetate layer is washed, dried, concentrated to dryness under reduced pressure, and crystallized from n-hexane-ethyl acetate to give 4-tert-butyl-N-{6-(2-hydroxy-ethyloxy)-5-(2-thienyl)-2-(2-pyrimidinyl)pyrimidin-4-yl}benzenesulfonamide (1790 mg) as a crystal.

M.p. 236°–237° C.
IR (nujol, cm⁻¹): 3450–3380, 1620
MS (m/z): 512 (M⁺)

REFERENCE EXAMPLE 7

(1) 5-(2-Methoxyphenoxy)-4,6-dichloro-2-(2-pyrimidinyl)pyrimidine and ethylene glycol are treated in the same manner as in Reference Example 1-(1) to give 2-{6-chloro-5-(2-methoxyphenoxy)-2-(2-pyrimidinyl)pyrimidin-4-yloxy}-ethanol (5.37 g) as a powder.
M.p. 133°–137° C.
IR (nujol, cm$^{-1}$): 3600–3300, 1650
MS (m/z): 474 (M$^+$)

(2) The above product (5.37 g) is treated in the same manner as in Reference Example 1-(2) to give 2-{6-azido-5-(2-methoxyphenoxy)-2-(2-pyrimidinyl) pyrimidin-4oyloxy}ethanol (1.29 g) as a powder.
M.p. 133°–134.5° C.
IR (nujol, cm$^{-1}$): 3430–3350, 2180, 2170, 1580
MS (m/z): 381 (M$^+$)

(3) The above product (1.29 g) is treated in the same manner as in Reference Example 1-(3) to give 2-{6-amino-5-(2-methoxyphenoxy)-2-(2-pyrimidinyl) pyrimidin-4-yloxy}ethanol (788 mg) as a powder.
M.p. 183.5°–185° C.
IR (nujol, cm$^{-1}$): 3590, 3450, 1620
MS (m/z): 355 (M$^+$)

(4) The above product (778 mg) is treated in the same manner as in Reference Example 3 to give 4-amino-6-[2-(5-bromopyrimidin-2-yloxy)ethoxy]-5-(2-methoxyphenoxy)-2-(2-pyrimidinyl)pyrimidine (733 mg) as a powder.
M.p. 124.5°–128.5° C.
IR (nujol, cm$^{-1}$): 3480, 3280, 1630
MS (m/z): 512 (M$^+$)

REFERENCE EXAMPLE 8

(1) To a solution of (2-methoxyphenoxy)malonic acid diethyl ester (10.0 g) and a 28% solution of sodium methoxide (3.83 g) in methanol (100 ml) is added urea (2.33 g) under warming, and the mixture is refluxed at 80° C. for 16 hours. After the reaction is completed, the solution is concentrated, and acidified with 10% hydrochloric acid. The precipitated crystals are collected by filtration, washed, and dried to give 5-(2-methoxyphenoxy)-2,4,6-trihydroxy-pyrimidine (7.10 g) as a crystalline powder.
M.p. 202°–204° C.
IR (nujol, cm$^{-1}$): 3500, 3180–2800, 1710
MS (m/z): 251 (M$^+$)

(2) A mixture of the above product (1.00 g), N-diethylaniline (1.28 ml) and phosphorus oxychloride (5 ml) is refluxed for three hours. The mixture is evaporated under reduced pressure to remove the phosphorus oxychloride, and the mixture is slowly poured into water. The mixture is stirred at room temperature, and extracted with ether. The extract is washed, dried, and evaporated under reduced pressure to remove the solvent. The residue is purified by silica gel column chromatography (solvent; hexane:ethyl acetate=30:1) to give 5-(2-methoxyphenoxy)-2,4,6-trichloropyrimidine (351 mg) as a crystal.
M.p. 150.5°–152° C.
IR (nujol, cm$^{-1}$): 1600
MS (m/z): 304 (M$^+$)

(3) To a solution of N-methylmorpholine (113.5 mg) in toluene (5 ml) is added a solution of the above product (300 mg) in toluene (5 ml) at 100° C., and the mixture is heated with stirring at 90° C. for two hours. After cooling, to the mixture is added water, and the mixture is extracted with ethyl acetate. The extract is washed, dried, and evaporated under reduced pressure to remove the solvent. The residue is crystallized from n-hexane to give 2-morpholino-4,5-dichloro-5-(2-methoxyphenoxy)pyrimidine (344 mg) as a powder.
M.p. 179.5°–180° C.
IR (nujol, cm$^{-1}$): 1600, 1540
MS (m/z): 355 (M$^+$)

(4) To a mixture of tetrahydrofuran (20 ml) and 2-benzyloxyethanol (3.66 g) is added sodium hydride (60% dispersion, 917 mg) at room temperature, and the mixture is stirred for 20 minutes. To the mixture is added dropwise a solution of the above product (7.78 g) in tetrahydrofuran-dimethylsulfoxide (30 ml), and the mixture is stirred at room temperature for one hour, and then stirred at 50° C. for two hours. The residue is dissolved in ethyl acetate, and the mixture is washed, dried, and concentrated to dryness under reduced pressure. The residue is purified by silica gel column chromatography (solvent; chloroform:ethyl acetate= 40:1 ) to give 6-(2-benzyloxyethoxy)-4-chloro-5-(2-methoxyphenoxy)-2-morpholinopyrimidine (6.61 g).
M.p. 133°–134.5° C.
IR (nujol, cm$^{-1}$): 1600, 1540–1520
MS (m/z): 472 (M$^+$)

(5) The above product (8.26 g) is treated in the same manner as in Reference Example 1-(2) to give 4-azido-6-(2-benzyloxyethoxy)-5-(2-methoxy-phenoxy)-2-morpholinopyrimidine (5.83 g) as a powder.
M.p. 146°–147.5° C.
IR (nujol, cm$^{-1}$): 2150, 1600
MS (m/z): 479 (M$^+$)

(6) The above product (5.83 g) is treated in the same manner as in Reference Example 1-(3) to give 2-{6-amino-5-(2-methoxyphenoxy)-2-morpholinopyrimidin-4-yloxy}ethanol (3.40 g) as a powder.
M.p. 136°–138.5° C.
IR (nujol, cm$^{-1}$): 3600–3200, 1630, 1600
MS (m/z): 363 (M$^+$)

(7) The above product (200 mg) is treated in the same manner as in Reference Example 3 to give 4-amino-6-[2-(5-bromopyrimidin-2-yloxy)ethoxy]-5-(2-methoxyphenoxy)-2-morpholinopyrimidine (290 mg) as a caramel.
IR (nujol, cm$^{-1}$): 3460–3100, 1600
MS (m/z): 519 (M$^+$)

REFERENCE EXAMPLE 9

(1) To a solution of (2-methoxyphenoxy)malonic acid diethyl ester (10.0 g) and thiourea (4.04 g) in methanol (100 ml) is added dropwise with stirring a 28% solution of sodium methoxide in methanol (17.07 g) over a period of 30 minutes under ice-cooling. The mixture is stirred at room temperature overnight. After the reaction is completed, the mixture is evaporated under reduced pressure to remove the solvent, and water (200 ml) is added to the residue. To the mixture is further added methyl iodide (3.30 ml), and the mixture is reacted at room temperature for three hours. The reaction solution is acidified with 10% aqueous hydrochloric acid, and the precipitated crystals are collected by filtration, washed with water, and dried to give 4,6-dihydroxy-5-(2-methoxyphenoxy)-2-methylthiopyrimidine (8.90 g).
M.p. 206°–210° C.

(2) A mixture of the above product (3.00 g), diethylaniline (5 ml) and phosphorus oxychloride (15 ml) is refluxed for two hours, and after the reaction is completed, the mixture is evaporated under reduced pressure to remove the phosphorus oxychloride. The resultant is poured into ice-water, and extracted with ethyl acetate. The extract is washed, dried, and concentrated to dryness under reduced pressure. The residue is crystallized from n-hexane to give 4,6-dichloro-5-(2-methoxyphenoxy)-2-methylthio-pyrimidine (2.67 g).

M.p. 148°–149.5° C.

(3) To a solution of the above product (1.0 g) in dimethylsulfoxide (10 ml) are added 4-tert-butylbenzenesulfonamide (705 mg) and potassium carbonate (1.31 g), and the mixture is heated with stirring at 70° C. for two hours. After cooling, the reaction mixture is treated with ice-water, and the mixture is acidified with 10% aqueous hydrochloric acid solution, and extracted with ethyl acetate. The extract is washed, dried, and evaporated under reduced pressure to remove the solvent. The residue is purified by silica gel column chromatography (solvent; chloroform:ethyl acetate=20:1), and recrystallized from ethyl acetate-n-hexane to give 4-tert-butyl-N-[6-chloro-5-(2-methoxyphenoxy)-2-methylthiopyrimidin-4-yl] benzenesulfonamide (1.14 g) as a crystal.

M.p. 123°–124° C.

(4) To ethylene glycol (11 ml) is added sodium hydride (60% dispersion, 441 mg), and thereto is added the above product (1.09 g). The mixture is heated at 80° C. for one hour, and then heated at 100° C. for three hours. After cooling, the reaction mixture is diluted with diluted hydrochloric acid under cooling, and extracted with ethyl acetate. The extract is washed, dried, and evaporated under reduced pressure to remove the solvent. The residue is purified by silica gel column chromatography (solvent; ethyl acetate:n-hexane=1:2), and recrystallized from ethyl acetate-n-hexane to give 4-tert-butyl-N-[6-(2-hydroxyethoxy)-5-(2-methoxyphenoxy)-2-methylthiopyrimidin-4-yl]-benzenesulfonamide (866 mg).

M.p. 139°–140.5° C.

(5) A solution of the above product (15.0 g) in tetrahydrofuran (150 ml) and dimethylacetamide (15 ml) ia added sodium hydride (60% dispersion, 3.46 g) in portions, and the mixture is stirred for 10 minutes. To the mixture is added 5-bromo-2-chloropyrimidine (8.36 g), and the mixture is stirred at room temperature for one hour. The reaction solution is poured into ice-water, and the mixture is neutralized with ammonium chloride, and extracted with ethyl acetate. The ethyl acetate layer is washed, dried, and evaporated under reduced pressure to remove the solvent. The residue is recrystallized from ethyl acetate-n-hexane to give N-{6-[2-(5-bromopyrimidin-2-yloxy)ethoxy]-5-(2-methoxyphenoxy)-2-methylthiopyrimidin-4-yl}-4-tert-butylbenzene-sulfonamide (16.42 g).

M.p. 117°–121° C.

(6) To a suspension of the above product (16.24 g) in chloroform (160 ml) is added m-chloroperbenzoic acid (85.4% purity, 10.67 g) under ice-cooling, and the mixture is reacted at 0° C. for one hour, and then reacted at room temperature for two hours. To the reaction solution is added aqueous sodium hydrogen sulfite solution, and the chloroform layer is separated. The chloroform layer is washed with water, dried, and evaporated under reduced pressure to remove the solvent. The residue is purified by silica gel column chromatography (solvent; chloroform:ethyl acetate= 20:1–3:1) to give N-[6-{2-(5-bromopyrimidin-2-yloxy)ethoxy}-5-(2-methoxyphenoxy)-2-methylsulfonyl-pyrimidin-4-yl]-4-tert-butylbenzenesulfonamide (13.45 g) as a caramel.

FAB-MS (m/z): 710, 708 (MH$^+$)

IR (nujol, cm$^{-1}$): 3170

REFERENCE EXAMPLE 10

(1) 4-tert-Butyl-N-[6-(2-hydroxyethoxy)-5-(2-methoxyphenoxy)-2-methyl-thiopyrimidin-4-yl] benzenesulfonamide (12.46 g) obtained in Reference Example 9-(4) is oxidized with m-chloroperbenzoic acid (10.66 g) in the same manner as in Reference Example 9-(6) to give 4-tert-butyl-N-[6-(2-hydroxy-ethoxy)-5-(2-methoxyphenoxy)-2-methylsulfonylpyrimidin-4-yl] benzene-sulfonamide (11.10 g) as a colorless caramel.

FAB-MS (m/z): 552 (MH$^+$)

(2) To a solution of the above product (1.00 g) and 3,4-dihydro-2H-pyran (350.8 mg) in methylene chloride (20 ml) is added 10-camphorsulfonic acid (21 mg), and the mixture is stirred at room temperature for two hours. The reaction solution is treated a diluted aqueous sodium hydrogen carbonate solution, and extracted with chloroform. The chloroform layer is washed with water, dried, and evaporated under reduced pressure to remove the solvent. The residue is recrystallized from methylene chloride-ethyl acetate to give 4-tert-butyl-N-{5-(2-methoxyphenoxy)-2-methylsulfonyl-6-[2-(terahydropyran-2-yloxy)ethoxy]pyrimidin-4-yl}benzenesulfonamide (790 mg) as a crystal.

M.p. 225°–227.5° C.

REFERENCE EXAMPLE 11

(1) To a solution of thiourea (13.69 g) in methanol (150 ml) is added a 28% solution of sodium methoxide in methanol (34.70 g) at 60° C., and thereto is further added (4-methylphenyl)malonic acid diethyl ester (32.62 g) at the same temperature. The reaction solution is refluxed for 8 hours. After cooling, water is added to the reaction solution, and the pH value of the solution is adjusted to pH 1 with hydrochloric acid under ice-cooing. The precipitated crystals are collected by filtration, and the residue is washed and dried to give 4,6-dihydroxy-2-mercapto-5-(4-methylphenyl) pyrimidine ( 12.53 g) as a crystal.

M.p. 290°–292° C.

(2) To a solution of the above product (12.5 g) and potassium carbonate (7.37 g) in dimethylsulfoxide (65 ml) is added methyl iodide (3.32 ml) at room temperature over a period of 10 minutes. The reaction is reacted at room temperature for two hours. Water is added to the reaction solution, and the mixture is acidified with hydrochloric acid under ice-cooling. The precipitated crystals are collected by filtration, and the residue is washed and dried to give 4,6-dihydroxy-5-(4-methylphenyl)-2-methylthiopyrimidine (10.56 g) as a crystal.

M.p. 226° C.–(decomposed)

(3) The above product (10.56 g) is treated in the same manner as in Reference Example 9-(2) to give 4,6-dichloro-5-(4-methylphenyl)-2-methylthio-pyrimidine (6.45 g) as a crystal.

M.p. 74.0°–78.0° C.

(4) The above product (6.45 g) and 4-tert-butylbenzenesulfonamide are treated in the same manner as in Reference Example 9-(3) to give 4-tert-butyl-N-[6-chloro-5-(4-methylphenyl)-2-methylthiopyrimidin-4-yl]benzenesulfonamide (7.31 g) as a crystal.

M.p. 178°–182° C.

(5) 2-Benzyloxyethanol (2.58 ml) is added dropwise to a suspension of sodium hydride (60% dispersion, 1.21 g) in tetrahydrofuran (60 ml) over a period of 10 minutes, and the mixture is stirred at room temperature for 10 minutes. To the reaction solution is added the above product (15.2 g), and the mixture is heated with stirring 50° C. for four hours. After cooling, the reaction solution is poured into iced aqueous hydrochloric acid solution, and the mixture is extracted with ethyl acetate. The extract is washed with water, dried, and evaporated under reduced pressure to remove the solvent. The residue is purified by silica gel column chromatography (solvent; n-hexane: ethyl acetate=30:1~10:1), and recrystallized from n-hexane to give N-[6-(2-benzyloxyethoxy)-5-(4-methylphenyl)-2-methylthiopyrimidin-4-yl]-4-tert-butyl-benzenesulfonamide (2.12 g).

M.p. 115°–116° C.

(6) The above product (2.10 g) is oxidized with m-chloroperbenzoic acid (1.84 g) in the same manner as in Reference Example 9-(6) to give N-[6-(2-benzyloxyethoxy)-5-(4-methylphenyl)-2-methylsulfonylpyrimidin-4-yl]-4-tert-butylbenzenesulfonamide (2.15 g) as a crystal.

M.p. 129°–130° C.

EFFECTS OF THE INVENTION

The desired compounds [I] of the present invention and a pharmaceutically acceptable salt thereof show high solubility in water, and excellent endothelin antagonistic activity so that they are useful in the prophylaxis or treatment of disorders associated with endothelin activities such as hypertension, pulmonary hypertension, renal hypertension, Raynaud disease, bronchial asthma, gastric ulcer, inflammatory bowl disease (Crohn's disease), shock, carcinogenesis, restenosis after angioplasty, organ dysfunction after transplantation, diabetes, thrombosis, arteriosclerosis, heart failure, chronic heart failure, acute renal insufficiency, glomerulonephritis, cyclosporin-induced nephrotoxicity, myocardial infarction, angina pectoris, arrhythmia, glaucoma, migraine, cerebrovascular spasm and cerebral infarction, and the like. Besides, the present compounds [I] and a pharmaceutically acceptable salt thereof are low toxic and hence, they show high safety as a medicament.

What is claimed is:

1. A sulfonamide derivative of the formula [I]:

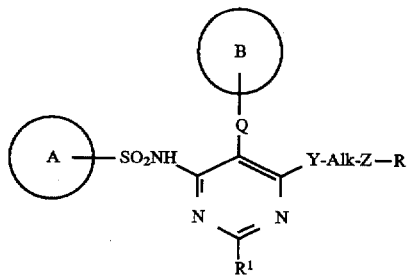

wherein Ring A and Ring B are a substituted or unsubstituted monocyclic, bicyclic or tricyclic hydrocarbon group, or a substituted or unsubstituted heterocyclic group, Q is a single bond or a group of the formula: —O—, —S—, —SO—, —SO$_2$— or —CH$_2$—, Y is a group of the formula: —O—, —S— or —NH—, Alk is a lower alkylene group or a lower alkenylene group, Z is a group of the formula: —O— or —NH—, R is a substituted or unsubstituted Nitrogen-containing aromatic heterocyclic or aryl group, R$^1$ is a hydrogen atom, a substituted or unsubstituted amino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group, or a pharmaceutically acceptable salt thereof.

2. The compound according to claim 1, wherein (1) Ring B is a substituted or unsubstituted bicyclic or tricyclic hydrocarbon group, or a substituted or unsubstituted heterocyclic group, when Ring A is a substituted or unsubstituted monocyclic hydrocarbon group, or (2) Ring B is a substituted or unsubstituted monocyclic, or bicyclic or tricyclic hydrocarbon group, or a substituted or unsubstituted heterocyclic group, when Ring A is a substituted or unsubstituted bicyclic or tricyclic hydrocarbon group, or a substituted or unsubstituted heterocyclic group; Q is a single bond or a group of the formula: —O—, —S—, —SO—, —SO$_2$— or —CH$_2$—; Y is a group of the formula: —O—, —S— or —NH—; Alk is a lower alkylene group or a lower alkenylene group; Z is a group of the formula: —O— or —NH—; R is a substituted or unsubstituted Nitrogen-containing aromatic heterocyclic or aryl group; R$^1$ is a hydrogen atom, a substituted or unsubstituted mono- or di-lower alkylamino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group.

3. The compound according to claim 2, wherein Ring A is a phenyl group substituted by a lower alkyl group or a lower alkylenedioxy group, and Ring B is a naphthyl group, a pyridyl group, a furyl group, a thienyl group which may optionally be substituted by a lower alkyl group, or a benzothienyl group, or Ring A is a naphthyl group which may optionally be substituted by a di-lower alkylamino group, an indenyl group, an anthryl group, a thienyl group which may optionally be substituted by a pyridyl group or a lower alkyl group, a benzofuryl group or a benzothienyl group, and Ring B is a phenyl group substituted by a lower alkyl group or a lower alkoxy group, a naphthyl group, a pyridyl group, a furyl group, a thienyl group which may optionally be substituted by a lower alkyl group, or a benzothienyl group; Q is a single bond or a group of the formula: —O—; Y is a group of the formula: —O—; Alk is a lower alkylene group; Z is a group of the formula: —O—; R is a pyrimidinyl group substituted by a group selected from a halogen atom, a thienyl group and a lower alkylthio group; R$^1$ is a hydrogen atom, a hydroxy-substituted lower alkylamino group, a lower alkyl group, a carboxy-substituted lower alkylthio group, a hydroxy-substituted lower alkoxy group, a pyrimidinyl group, a hydroxy-substituted piperidyl group, a lower alkyl-substituted piperazinyl group or a morpholino group.

4. The compound according to claim 3, wherein Ring A is a phenyl group substituted by a lower alkyl group or a lower alkylenedioxy group, and Ring B is a naphthyl group, a pyridyl group, a furyl group, a thienyl group which may optionally be substituted by a lower alkyl group, or a benzothienyl group, or Ring A is a naphthyl group which may optionally be substituted by a di-lower alkylamino group, an indenyl group, an anthryl group, a thienyl group which may optionally be substituted by a pyridyl group or a lower alkyl group, a benzofuryl group or a benzothienyl group, and Ring B is a phenyl group substituted by a lower alkyl group or a lower alkoxy group, or a thienyl group substituted by a lower alkyl group.

5. The compound according to claim 1, wherein Ring A and Ring B are a substituted or unsubstituted phenyl group, Q is a single bond or a group of the formula: —O—, Y is a group of the formula: —O—, Alk is an ethylene group, X is a group of the formula: —O—, R is a substituted or unsubstituted aromatic heterocyclic group, $R^1$ is a substituted or unsubstituted amino group, a substituted or unsubstituted lower alkyl group, a substituted or unsubstituted lower alkoxy group, a substituted or unsubstituted lower alkylthio group, or a substituted or unsubstituted nitrogen-containing heterocyclic group.

6. The compound according to claim 5, wherein Ring A is a phenyl group substituted by a lower alkyl group, Ring B is a phenyl group substituted by a lower alkyl group or a lower alkoxy group, R is a pyrimidinyl group substituted by a group selected from a halogen atom, a lower alkyl group, a hydroxy-lower alkyl group, a lower alkoxy group, a phenyl group, a furyl group, a thienyl group and a pyridyl group; $R^1$ is an amino group which may optionally be substituted by 1 to 2 groups selected from a mono- or di-hydroxy-lower alkyl group, a lower alkyl group, a lower alkoxy group, an amino-lower alkyl group, a mono- or di-lower alkylamino-lower alkyl group, a lower alkoxy-lower alkyl group and a carboxy-lower alkyl group; a lower alkyl group substituted by a carboxyl group or a hydroxyl group; a lower alkoxy group which may optionally be substituted by a group selected from a hydroxyl group, a carboxyl group, a hydroxy-lower alkyl group, a carboxy-lower alkyl group, an amino-lower alkyl group and a mono- or di-lower alkylamino group; a lower alkylthio group which may optionally be substituted by a group selected from a hydroxyl group, a carboxyl group, a lower alkoxycarbonyl group, an amino group and a mono-or di-lower alkylamino group; a piperidyl group which may optionally be substituted by a group selected from a hydroxyl group, a carboxyl group, an amino group and a mono-or di-lower alkylamino group; or a tetrazolyl group.

7. The compound according to claim 6, wherein R is a pyrimidinyl group substituted by a halogen atom or a lower alkoxy group, $R^1$ is an unsubstituted amino group or an amino group substituted by 1 to 2 groups selected from a mono- or di-hydroxy-lower alkyl group, a mono- or di-lower alkylamino-lower alkyl group and a lower alkoxy-lower alkyl group.

8. N-[6-[2-[(5-Bromopyrimidin-2-yl)oxy]ethoxy]-2-(4-hydroxypiperidino)-5-(2-methoxyphenyloxy)pyrimidin-4-yl]-4-tert-butylbenzenesulfonamide, or a pharmaceutically acceptable salt thereof.

9. N-[2-[(2-Methoxyethyl)amino]-5-(2-methoxyphenyloxy)-6-[2-[(5-methoxypyrimidin-2-yl)oxy] ethoxy]pyrimidin-4-yl]-4-tert-butylbenzenesulfonamide, or a pharmaceutically acceptable salt thereof.

10. N-[6-[2-[(5-Bromopyrimidin-2-yl)oxy]ethoxy]-2-[(2-hydroxyethyl)amino]-5-(4-methylphenyl)pyrimidin-4-yl]-4-tert-butylbenzenesulfonamide, or a pharmaceutically acceptable salt thereof.

11. A process for preparing a sulfonamide derivative of the formula [I]:

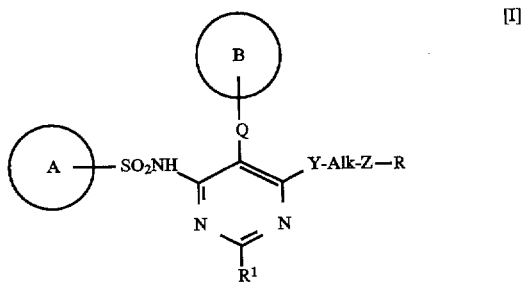

wherein Ring A and Ring B are a substituted or unsubstituted monocyclic, bicyclic or tricyclic hydrocarbon group, or a substituted or unsubstituted heterocyclic group, Q is a single bond or a group of the formula: —O—, —S—, —SO—, —SO$_2$— or —CH$_2$—, Y is a group of the formula: —O—, —S— or —NH—, Alk is a lower alkylene group or a lower alkenylene group, Z is a group of the formula: —O— or —NH—, R is a substituted or unsubstituted nitrogen-containing aromatic heterocyclic or aryl group, $R^1$ is a hydrogen atom, a substituted or unsubstituted amino group, a substituted or unsubstituted lower alkyl group, a substituted or unsubstituted lower alkenyl group, a substituted or unsubstituted lower alkynyl group, a substituted or unsubstituted lower alkylthio group, a substituted or unsubstituted lower alkoxy group, or a substituted or unsubstituted heterocyclic group or a substituted or unsubstituted aryl group, or a pharmaceutically acceptable salt thereof, which comprises reacting a compound of the formula [VI]:

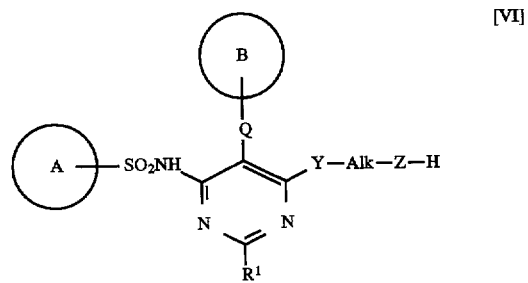

wherein the symbols are the same as defined above, or a salt thereof, with a compound of the formula [VII]:

wherein $X^3$ is a reactive residue and the other symbol is the same as defined above, and if necessary, followed by converting the product into a pharmaceutically acceptable salt thereof.

* * * * *

UNITED STATES PATENT AND TRADEMARK OFFICE
CERTIFICATE OF CORRECTION

PATENT NO. : 5,739,333
DATED : April 14, 1998
INVENTOR(S) : Koichiro YAMADA et al.

It is certified that error appears in the above-identified patent and that said Letters Patent is hereby corrected as shown below:

Claim 5, column 67, line 17, after "unsubstituted", insert --nitrogen-containing--.

Claim 5, column 67, lines 21-22, after "unsubstituted", delete "nitrogen-containing".

Signed and Sealed this

Eighth Day of December, 1998

Attest:

BRUCE LEHMAN

Attesting Officer

Commissioner of Patents and Trademarks